(12) United States Patent
Sumner, II et al.

(10) Patent No.: US 7,725,328 B1
(45) Date of Patent: May 25, 2010

(54) COMPUTER ARCHITECTURE AND PROCESS OF PATIENT GENERATION EVOLUTION, AND SIMULATION FOR COMPUTER BASED TESTING SYSTEM

(75) Inventors: Walton Sumner, II, Webster Groves, MO (US); Jin Zhong Xu, Lexington, KY (US); Guy H. Roussel, Lexington, KY (US); Michael D. Hagen, Lexington, KY (US)

(73) Assignee: American Board of Family Practice, Inc., Lexington, KY (US)

( * ) Notice: Subject to any disclaimer, the term of this patent is extended or adjusted under 35 U.S.C. 154(b) by 1471 days.

(21) Appl. No.: 10/704,528

(22) Filed: Nov. 7, 2003

Related U.S. Application Data

(63) Continuation-in-part of application No. 09/759,205, filed on Jan. 16, 2001, now Pat. No. 6,978,244, which is a continuation of application No. 08/961,185, filed on Oct. 30, 1997, now Pat. No. 6,246,975.

(60) Provisional application No. 60/029,856, filed on Oct. 30, 1996.

(51) Int. Cl.
*G06Q 10/00* (2006.01)
(52) U.S. Cl. .................... 705/2; 705/3; 600/300; 600/301
(58) Field of Classification Search ............. 705/2–4; 600/300, 301
See application file for complete search history.

(56) References Cited

U.S. PATENT DOCUMENTS

| | | | | |
|---|---|---|---|---|
| 4,315,309 | A | * | 2/1982 | Coli ............................ 705/3 |
| 5,005,143 | A | * | 4/1991 | Altschuler et al. ............ 702/181 |
| 5,583,758 | A | * | 12/1996 | McIlroy et al. ................ 705/2 |
| 5,961,332 | A | * | 10/1999 | Joao ............................ 434/236 |
| 6,246,975 | B1 | | 6/2001 | Rivonelli et al. |

OTHER PUBLICATIONS

Charniak, Bayesian Networks without Tears, AI Magazine, Winter 1991, p. 50-63.

Haddawy et al., Generating Explanations and Tutorial Problems from Bayesian Networks, AMIA, Inc., 1994, p. 770-774.

Haddawy et al., Clinical Simulation using Context-Sensitive Temporal Probability Models, AMIA, Inc., 1995, p. 203-207.

Shahar et al., Semi-automated Entry of Clinical Temporal-abstraction Knowledge, Journal of the American Medical Informatics Association, Nov./Dec. 1999, p. 494-511, vol. 6 No. 6.

Shahar et al., A Temporal-Abstraction System for Patient Monitoring, Stanford University School of Medicine, Standord, California.

(Continued)

*Primary Examiner*—Gerald J. O'Connor
*Assistant Examiner*—Rajiv J Raj
(74) *Attorney, Agent, or Firm*—James C. Eaves, Jr.; Greenebaum Doll & McDonald PLLC; Brian W. Chellgren

(57) ABSTRACT

The present invention relates to a computer implemented system and method for generating and interacting with a multi-factoral patient simulation responsive to user queries and interventions.

25 Claims, 12 Drawing Sheets

OTHER PUBLICATIONS

Shahar et al., Temporal-Abstraction Mechanisms in Management of Clinical Protocols, Stanford University School of Medicine, Stanford, California.

Sumner et al., Modeling Fatigue, AMIA 2002 Annual Symposium Proceedings, p. 747-751.

Sumner et al., Simulating Patients with Parallel Health State Networks, AMIA, Inc., 1998, p. 438-442.

Sumner et al., A Revolution in the Assessment of Clinical Knowledge, JABFP, Jan.-Feb. 1996, p. 41-52, vol. 9 No. 1.

* cited by examiner

COMPUTER ARCHITECTURE AND PROCESS OF PATIENT GENERATION EVOLUTION, AND SIMULATION FOR COMPUTER BASED TESTING SYSTEM

This continuation-in-part application claims priority from U.S. patent application Ser. No. 09/759,205 entitled COMPUTER ARCHITECTURE AND PROCESS OF PATIENT GENERATION, EVOLUTION, AND SIMULATION FOR COMPUTER BASED TESTING SYSTEM to Rovinelli, et al., filed Jan. 16, 2001, now U.S. Pat. No. 6,978,244 hereby incorporated by reference, which is a continuation of U.S. patent application Ser. No. 08/961,185 filed Oct. 30, 1997, now U.S. Pat. No. 6,246,975 which in turn claims priority from U.S. Provisional Patent Application No. 60/029,856 filed Oct. 30, 1996, both of which are herein incorporated by reference.

FIELD OF THE INVENTION

The instant invention relates generally to a computer implemented system and method for patient generation, evolution, and simulation, and particularly to a computer implemented system and method for patient generation, evolution, and simulation for a computer based testing system wherein the patient provides detailed temporally and physiologically reasonable responses to queries or interventions submitted by a user. The present invention is also suitable for simulation of a plurality of complex systems, such as plants, animals, machines, and even entire populations.

BACKGROUND OF THE RELATED ART

Prior art physician certifying systems have traditionally relied upon written cognitive examinations as a method for the assessment of the candidate's (diplomate's) medical knowledge, or alternatively, oral examinations. Test formats such as multiple choice questions have well-defined operating characteristics and are reliable for determining a candidate's cognitive functioning in the test subject area.

However, these tools generally measure only cognitive knowledge, and provide at best a primitive ability to assess a candidate's problem-solving abilities.

Prior art physician assessment processes suffer from several disadvantages: 1) test development requires re-generation of an examination with new material on a recurring (usually annual) basis; 2) the use of multiple choice testing for assessing clinical problem solving is sub-optimal; and 3) the tests are generally incapable of presenting patients with symptoms responsive to physician interventions.

A plurality of computer programs and associated models have been constructed to simulate patient-physician interaction. However, many of these programs suffer from the problem that the clinical simulations are "hard-wired" in computer source code and thus must be reprogrammed for each new examination. Once a simulation is used widely, the examination is no longer secure thereby necessitating further simulation development.

Furthermore, prior art simulators are largely incapable of providing for interaction between a physician and a simulated patient. While some systems provide the ability for a simulated patient to present a symptom, and provide a rudimentary response to a user supplied intervention these systems do not have the ability to intelligently respond to a simple physician question such as, "Do you have pain anywhere?" and a follow-up detail question such as "What alleviates your pain?"

Responsive to the aforementioned disadvantages in the prior art, a computer implemented system and method for patient simulation that is capable of interacting with a user-physician is provided. The system is capable of instantiating medical knowledge as object-oriented data structures known as a knowledge base of family medicine, utilizing the medical knowledge structures to generate realistic clinical scenarios (simulated patients), accepting queries and interventions from a user based on symptoms presented by the simulated patient, provide detailed symptom descriptions to the user that are temporally and physiologically reasonable, and assess the candidate's clinical problem solving ability by determining the response to the simulated patient of a prescribed intervention.

One difficulty encountered when providing for simulation of patients for diagnostic purposes is the development of temporal events in a simulated patient such that a diagnosing physician may inspect the duration of events that impinge on the simulated patient's health and be presented with temporally reasonable reports that are descriptive of how a patient would feel given those events. In other words, a sophisticated patient simulator should be able to construct and present patient symptom histories that are both physiologically and temporally reasonable given the patient's health state and any interventions or courses of action that may have been prescribed by a diagnostician. Additionally, the modeling of concurrent diseases in the same patient requires the simulator to distinguish findings or patient symptoms that may be identical or substantially similar for the concurrent diseases, but require dissimilar treatment from the treating physician.

Furthermore, to enhance the ability of a system to examine diagnostic and health management skill sets, the system should simulate a patient that has the ability to communicate the presence of pain (a site), and the palliative, provocative, quality, radiation, severity and temporal details thereof. These details are sometimes referred to as the "PQRST" symptom details.

Thus a robust system should enable a simulated patient to include the presence or absence of a health problem, any findings related thereto, and the existence and effects of any interventions, prescribed or otherwise, over time. The patient simulator could then inspect these details and produce reports to the user that are temporally reasonable given the patient's history.

Prior art systems of patient simulation and interaction are generally incapable of producing a response to user queries that adequately describes the effects of provocative and palliative events over time, or even reasonably describes the net results of multiple events that may interact with each other. For example, the question "During an angina attack, what relieves your pain?" restricts any reasonable response from the simulator to the chest area, or wherever the simulated patient is feeling the angina, and the time to "during an angina attack". While the query itself is detailed in its nature, it lacks a specific reference to time (and is of course nonsensical absent some angina in the simulated patient).

Furthermore, the user's query may require that the simulated patient summarize the overall results of multiple events such as angina attacks. In such a case, a complete response may include multiple parts, which may not be logically possible when taken separately. For example, in response to a query regarding angina over time, a patient may respond thusly: "Rest completely relieves my pain in about 20 minutes. Nitroglycerin completely relieves my pain in a few minutes, but not if I continue to exercise." This response includes details about the patient's level of relief and how quickly it occurs under certain circumstances. Additionally, in order for the response to present a complete picture of the patient's pain, several details must be appended together.

Previously described mechanisms for answering queries (e.g. Sumner W., Hagen M D, Rovinelli R. The item generation methodology of an empiric simulation project, Advances in Health Sciences Education 1999; 4(1):25-35) severely limit a patient simulator's ability to adapt to important variables. A simple and obvious mechanism for describing temporal details is to record data such as the time that a health state begins during the generation of a virtual patient, then report the time elapsed since the health state began as a temporal feature of the patient. For instance, if the health state is hypothyroidism, and the user asks about fatigue, the simulator could report the duration of the virtual patient's hypothyroidism as a surrogate for the duration of fatigue. Similarly, the simulator could instantiate the hypothyroid state by asserting a fatigue score. This method, however, is inadequate to describe the end result of several diseases or several interventions affecting one symptom. For instance, a virtual patient portraying anemia, hypothyroidism, and depression may report fatigue, but the fatigue should not respond to any single treatment. Only simultaneous treatment of hypothyroidism, resolution or treatment of depression, and completed treatment of anemia should eliminate fatigue.

These variables may include the user's selection of interventions, the timing and strength or dose of those interventions, and the interaction of multiple diseases and interventions over time. Other important variables include the interval between queries, recall of previous query results, and descriptions of responses to individual interventions apart from the overall mixture of interventions. The invention described herein provides methods for each of these purposes.

SUMMARY OF THE INVENTION

The computer-implemented system and method described herein utilizes knowledge at multiple levels of complexity. A disease is represented as a series of Health States, for example from Normal (Non-reactive) Airways, Reactive Airways-Mild, Reactive Airways-Moderate, and Reactive Airways-Severe. Each Health State contains identifiers which relate the particular Health State to precedents and antecedents, e.g., Normal Airways serves as the precursor Health State for Mild Reactive airways disease, and Mild, Moderate and Severe Reactive Airways Disease represent target Health States from the Normal circumstance.

Each Health State in turn has associated Findings, and specific Findings. Referring again to our prior example, the Normal Airways state, the Finding "Shortness of Breath" is instantiated with the Specific Finding "No shortness of breath." Similarly, other Findings such as Respiratory Function and Severe Asthma Attack Frequency are instantiated with corresponding normal Specific Findings (Normal Respiratory Functions, and No Severe Attacks.)

The system and method of the present invention partitions knowledge into the following types: Health States, Agents, Findings, Specific Findings and Patterns describe system behaviors and characteristics. Courses-of-Action may include interventions such as prescriptions, procedures, advice, referrals for further opinions, etc., and are a class of objects descriptive of human activities. Furthermore, Query objects are used by the invention to correspond to user queries, laboratory tests, images, physical examinations, referrals for opinions and the like which evaluate Health State information and characteristics described in the model. Subdivision of knowledge types in this manner facilitates the process of acquiring knowledge and further promotes multiple levels of knowledge abstraction, which enhances the system's ability to represent varying levels of complexity in its modeling process. Multiple levels of abstraction and types of knowledge require the use of a plurality of viable methodologies for collecting knowledge data, including direct questioning of domain experts/protocol analysis. The System and Method of the present invention includes a blend of these approaches. Direct questioning is used in querying family medicine physicians regarding their knowledge of and approaches to specific knowledge domains. Additionally, knowledge acquisition includes access to appropriate scientific literature, which serves to provide an ethnographic assay of actual practice. Knowledge acquisition also entails protocol analysis, both in terms of analyzing specific physicians' problem solving methodologies and incorporating clinical processes such as those presented in published clinical guidelines.

The computer-implemented invention is divided into three components: a knowledge base, a patient simulation generator, and a presentation system. The knowledge base is designed and represented as a series of entity-relationships. The knowledge base model has a plurality of fundamental entities: Patient, Health States, Findings, Courses of Action, Queries, and Agents. In turn, these entities have the following relationships: INTERACTS WITH, CONTACTS, RELATED TO, EXHIBITS, USE, HAS, DEFINES, DEFINES VALUES, ABSTRACTS, INCLUDES, EXPOSED TO, and LEADS TO.

FIG. 1 depicts an exemplary conceptual view of the entities and relationships included in the knowledge base model in accordance with one embodiment of the invention. Rectangles indicate entities in the model. Diamonds indicate relationships.

The computer-implemented patient simulator of the present invention employs upon a series of generation methods to instantiate patients for presentation to a certification/re-certification candidate typically referred to as a user or physician throughout this specification. The processes evolve the patient forward (to reflect progression of the disease process and response to interventions) and backward in time (to create a past history for the patient). To accomplish these tasks, the system defines processes for:

Content specification—to define the scope of the simulation;

Patient generation—both backwards and forwards to produce a medical history past, present and future; and Simulation processes—for presentation of the patient findings developed from generation processes.

Additionally, book-keeping processes are defined for evaluating a user's responses and patient evolution.

The system and method of the present invention produces a patient description which reflects the EXHIBITS, HAS, INTERACTS-WITH, EXPOSED-TO, IS-RELATED, and CONTACTS relationships described above. These generated entity relations are stored as a collection of records in the patient simulator. These records serve as inputs to the patient evolution process, which evolves the patient's health status and medical/personal characteristics as a function of the passage of time or user intervention. The patient generation process is called once at a session's start. In contradistinction, the system calls the evolution process repeatedly in response to time progression and physician action.

Referring to FIGS. 3 and 4, and in accordance with one embodiment of the invention, the first phase of patient generation is developing the patient's history outline. This outline describes the series of health states and risk factors the patient experienced to reach the current health state, TS. The system first establishes the simulated patient's age at presentation (and therefore age), the patient's sex and racial/ethnic origin. A separate process then assigns the simulated patient a name.

Once the patient's age, sex, racial/ethnic origin, and age at onset of the condition are established, the OutlineFirstStep procedure defines a plurality of precursor states and risk factors for evolving the patient to the current time and target health state. An OutlineGeneralStep procedure is then called iteratively until the patient has arrived at the current TS. These processes are described in greater detail below.

The database further comprises a plurality of small inference programs for example, Bayesian networks describing a generation method, or Bayesian networks describing a transition time, that are utilized for the generation process described above. In this implementation, a Bayesian network's nodes are divided into lists of input nodes, which read from the simulated patient; intermediate nodes, which make inferences about the simulated patient or calculate values based on the values or states of other nodes; and output nodes, which write information to the simulated patient. Also, in the current invention it is advantageous to identify a node of a Bayesian network as a root node wherein the state of that node generally provides a synopsis of the solution to the entire network. Input and intermediate Bayes nodes may be continuously or discretely valued. Continuously valued nodes acquire a numeric value by one of several mechanisms; the value acquired determines the state of the node. Discrete node state are defined by categorical statements about characteristics of a simulated patient, or stochastic inferences, but not by a number. Accordingly, each node state will have its' own unique definition, which may or may not be related to the definitions of other states of the same node. Additionally, these inference programs are used throughout the present invention to maintain consistency between previously specified data pertaining to the simulated patient, and new data. For example, during patient generation and evolution, Bayesian networks may determine how quickly health states should change, based on the patient's age, concurrent health problems, and relevant interventions. The Bayesian networks may also be employed to control the simulator's responses to user queries and the selection of Findings and Specific Findings which are germane to the queries and indicative of core manifestations of the patient's Health State. When a Specific Finding includes values (for some physiological variable) that vary with time, an inference program controls the selection of a series of time-value pairs representative of a Pattern. These Patterns in turn are interpreted to provide a description of Specific Findings responsive to the user queries for information.

The presentation system displays a patient description (age, race, sex, clinical findings) to the user, who may then select appropriate COA's for further management of the patient's health.

A COA can modify the duration of a Health State in which a patient exists at a point in time. When the candidate selects such a COA, the simulated patient is evolved to a new Health State employing the patterns associated with the new Health State in the knowledge base. Health States closely associated with each other are represented as parallel Health States not as combined Health State entities.

As one example, an initial patient having a case of osteoarthritis might demonstrate mild osteoarthritis. However, other Health States, such as obesity, might influence the progress of the patient's arthritis from mild to moderate or severe disease. To avoid combinatoric Health State explosion, the invention employs a parallel network of Health States. A newly-generated patient will exhibit instantiated Health State patterns for a primary domain (in this case osteoarthritis) and for the plurality of parallel Health States (obesity in this example) which influence the primary Health State's progress.

Osteoarthritis may progress over time from a normal state to mild, moderate or severe osteoarthritis. For this particular illness, progress occurs in one direction only; osteoarthritis does not regress once developed, but can stabilize at a particular degree of severity. Obesity represents a parallel Health State which can influence the progression of osteoarthritis. Mild, moderate, and severe obesity can influence this progress at different rates: the model permits representation of greater impact for more severe obesity states. Notice also that obesity can regress (e.g., severe obesity can revert to moderate obesity, etc.).

Additionally, any one of a number of parallel Health States might exist which could progress independently of the osteoarthritis Health State. For example, the patient who has osteoarthritis will frequently use non-steroidal anti-inflammatory drugs (NSAID's) for treatment.

The present invention provides an exemplary process for developing domain-specific knowledge. A template for each knowledge domain includes the following hierarchy:

| | |
|---|---|
| HEALTH STATE: | {name assigned by the knowledge donor, e.g., "Normal Airway Reactivity"} |
| PREVALENCE: | {age-sex-race specific prevalence; represented as pattern} |
| INCIDENCE: | {age-sex-race specific incidence; represented as pattern} |
| FINDING: | {general name for set of findings, e.g., "Asthma Attack Frequency" in reactive airways disease} |
| SPECIFIC FINDING: | {description of specific instance of a FINDING; e.g., for the FINDING of asthma attack frequency, one specific finding is "No Attacks", associated with "Normal Airway Reactivity"} |

Each HEALTH STATE affects multiple FINDINGS, which in turn have Specific Findings appropriate for that FINDING in that HEALTH STATE. Data such as incidence, prevalence, and attack rates are represented as PATTERNS (graphical functions which support the patient generation simulation processes). The information is collected in template form, often using an XML template or the equivalent thereof, and then transferred into computer-readable format using, for example, any standard Knowledge Acquisition (KA) tool to enter the information into an object-oriented database.

The knowledge acquisition step includes the following subcomponents:

A. Health State specification;

B. Enumeration of FINDINGs for the Health State, and agreement among the development team members;

C. Gathering information pertaining to relevant temporal data from literature, or solicitation of expert opinion;

D. Entry of Health State knowledge into knowledge base using KA tool;

E. Debugging, including generating multiple simulations, to test system stability/credibility F. Validation including review of generated cases by representative groups of family physicians.

Accordingly, one object of the present invention is a system that allows testing of users at remote sites and creates temporally reasonable answers to questions at test sites.

It is another object of the present invention to provide a computer-implemented testing system that permits a user to receive detailed symptom information from a generated patient.

It is another object of the present invention to provide a formal model of family medicine to achieve a relevant and realistic implementation of a computer based examination.

A yet further object of the present invention is a system and method for generating a simulated patient responsive to a user query regarding health symptoms that includes details on palliative, provocative, qualitative, radiation, severity and temporal factors of a patient's symptoms;

A yet further object of the present invention is a system and method for producing a detailed response to a user query regarding a simulated patient's condition that is reasonable both temporally and physiologically.

It is to be understood that the present invention is not limited in its application to the details of construction and to the arrangements of the components set forth in the following description or illustrated in the drawings. The invention is capable of other embodiments and of being practiced and carried out in various ways. Furthermore, the terminology employed herein are for the purpose of description and should not be regarded as limiting.

Further objects, features, and advantages of the present invention, and a better understanding thereof will be made readily apparent when reading the detailed description of the preferred embodiments herein below, as well as by reference to the accompanying drawing Figures wherein like numerals refer to like elements throughout.

NOTATIONS AND NOMENCLATURE

Figure 1:
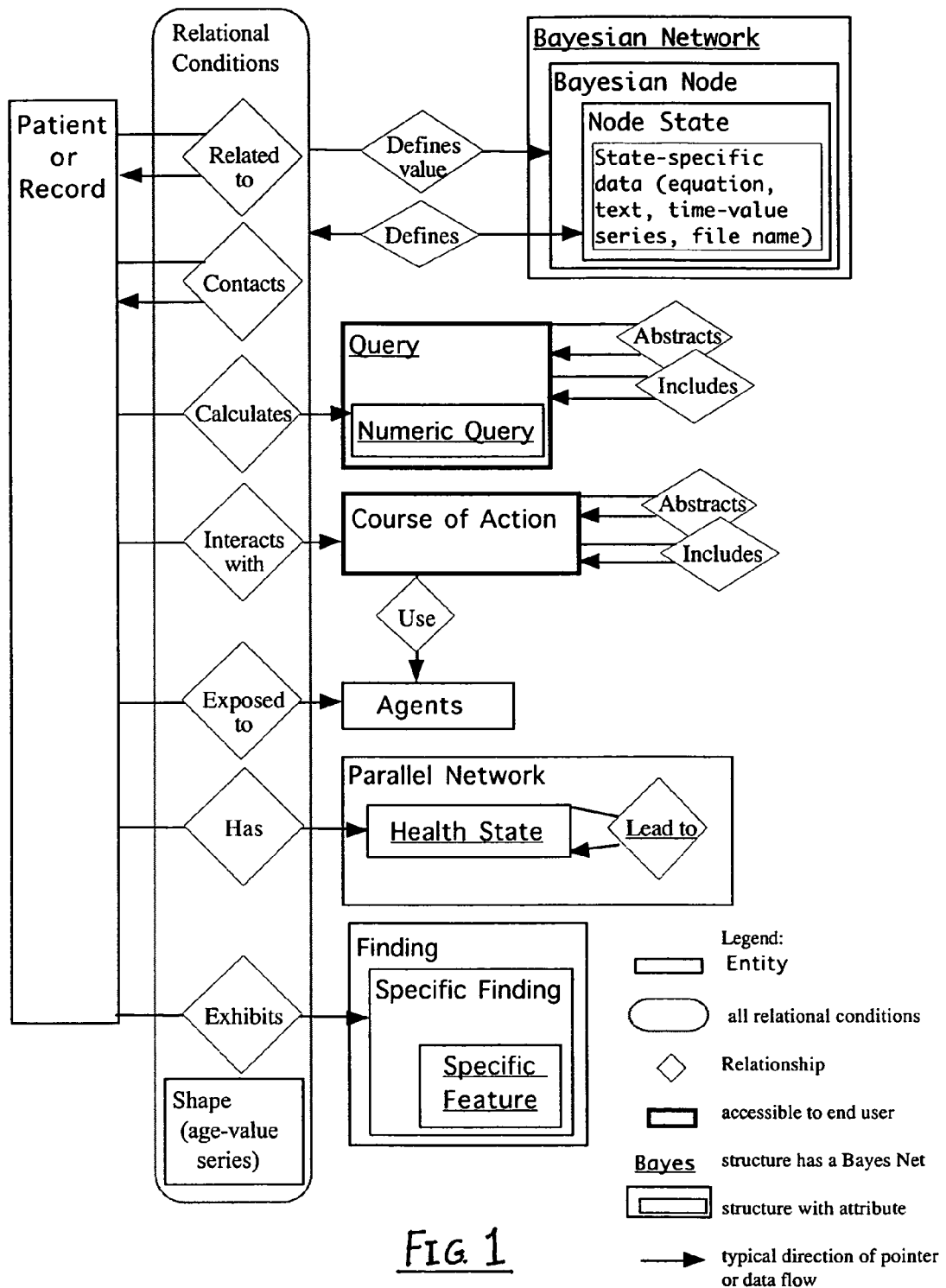
FIG. 1 is a diagram describing an overall or conceptual view of the entities and relationships in the model used in the computer based examination system of the present invention.
Figure 2:
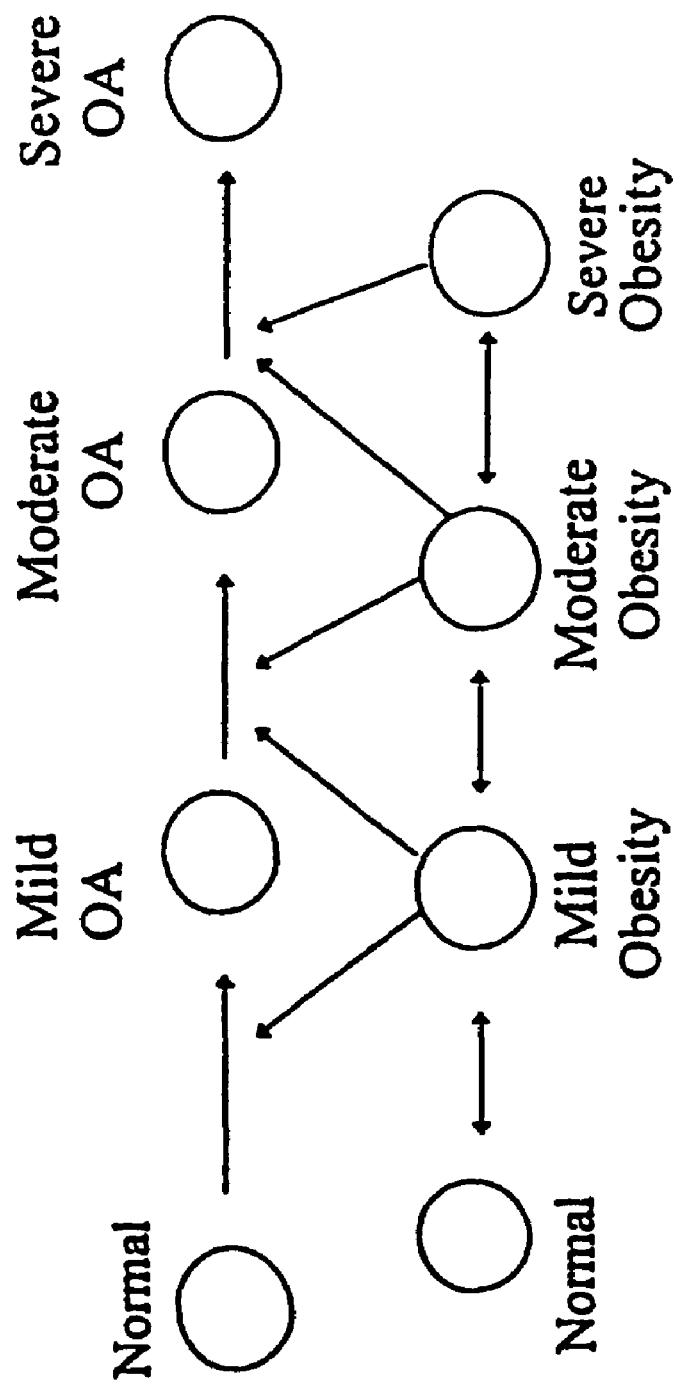
FIG. 2 is a diagram describing the progression of osteoarthritis over time from the normal state to mild, moderate or severe states of osteoarthritis in a comorbid network with obesity in accordance with one feature of the invention.
Figure 3:
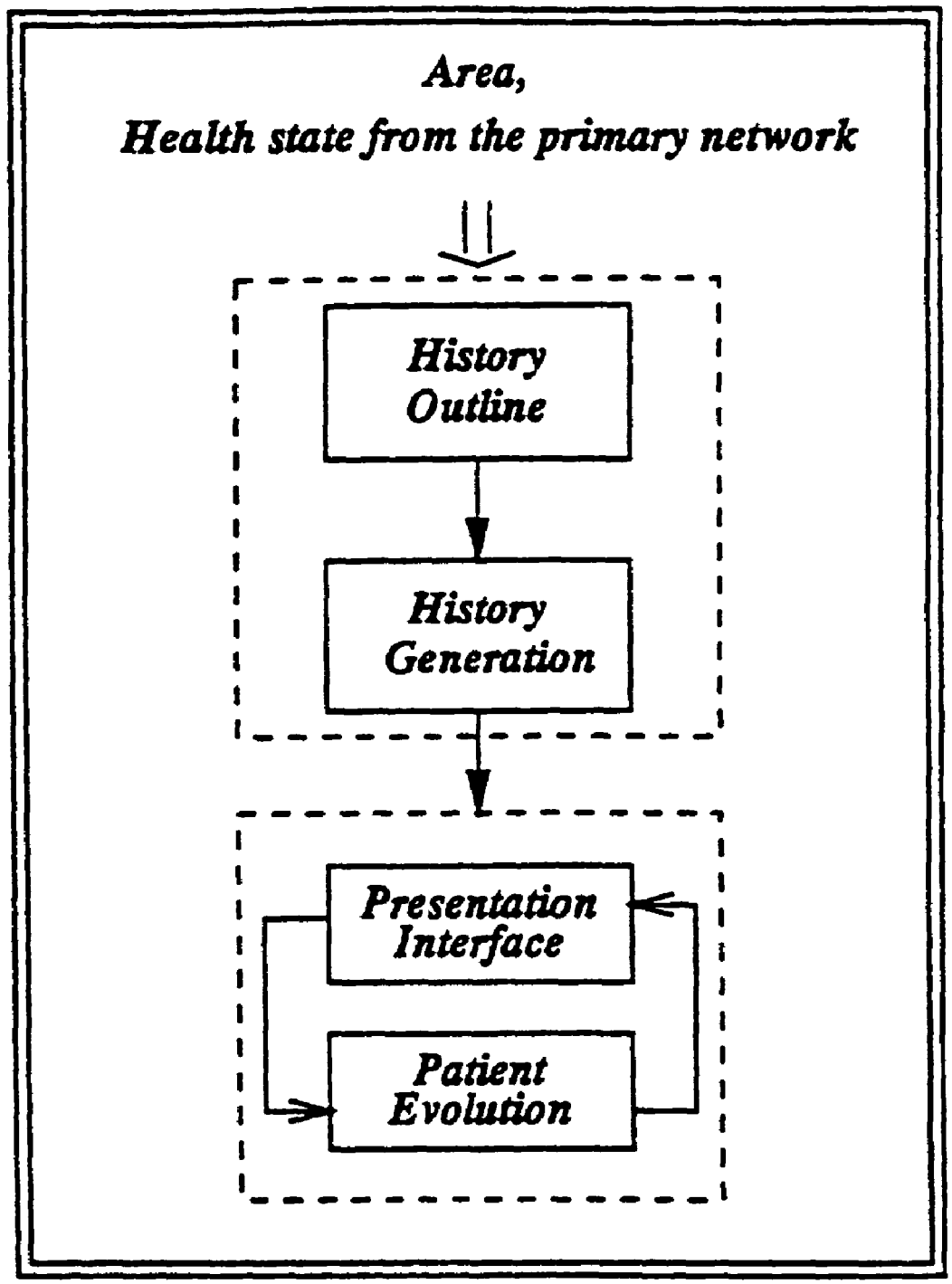
FIG. 3 is a block diagram of a patient history generation and presentation to a user in accordance with the present invention.

The detailed descriptions which follow may be presented in terms of program procedures executed on a computer or network of computers. These procedural descriptions and representations are the means used by those skilled in the art to most effectively convey the substance of their work to others skilled in the art.

A procedure is a self-consistent sequence of steps leading to a desired result. These steps are those requiring physical manipulations of physical quantities. Usually, these quantities take the form of electrical or magnetic signals capable of being stored, transferred, combined compared and otherwise manipulated. It proves convenient at times, principally for reasons of common usage, to refer to these signals as bits, values, elements, symbols, characters, terms, numbers, or the like. All these and similar terms are to be associated with the appropriate physical quantities and are merely convenient labels applied to these quantities.

Further, the manipulations performed are often referred to in terms, such as adding or comparing, which are commonly associated with mental operations performed by a human operator. No such capability of a human operator is necessary, or desirable in most cases, in any of the operations described herein which form part of the present invention; the operations are machine operations. Useful machines for performing the operation of the present invention comprise general purpose digital computers or similar devices.

The present invention also relates to apparatus for performing these operations. This apparatus may be specially constructed for the required purpose or it may comprise a general purpose computer as selectively activated or reconfigured by a computer program stored in the computer. The procedures presented herein are not inherently related to a particular computer or other apparatus. Various general purpose machines may be used with programs written in accordance with the teachings herein, or it may prove more convenient to construct more specialized apparatus to perform the required method steps. The required structure for a variety of these machines will appear from the description given.

DETAILED DESCRIPTION OF THE PREFERRED EMBODIMENTS

The computer-implemented testing system and method described in detail herein models knowledge at multiple levels of complexity by partitioning said knowledge into fundamental types: Health States, Agents, Findings, Specific Findings, Patterns and Sub-patterns describe system behaviors and characteristics. Courses-of-Action describe tasks and methods used to modify the Health State information and characteristics described in the model such as Health State progression and manifestations. Queries (sometimes called "Reveals") evaluate Health State information and characteristics, and determine what data to present to a user.

Each Health State has associated Findings, and Specific Findings. For example, in a Normal Airways state, "Asthma Attack Frequency" appears as a Finding which is instantiated with the Specific Finding "No attacks." Similarly, other Findings such as Respiratory Function and Severe Asthma Attack Frequency are instantiated with corresponding normal Specific Findings (Normal Respiratory Functions, and No Severe Attacks.)

The examination or recertification process is as follows. After initial certification, users initiate re-certification software on a workstation computer system. The user begins re-certifying at any convenient time and may suspend the examination at the conclusion of a simulated patient encounter. The present invention presents a patient using text, illustrations, still pictures, and even video via a graphical user interface (GUI). The user queries and examines the simulated patient, reaches conclusions, and prescribes treatment options. The simulated patient may express preferences about these options.

After receiving a treatment plan, the patient "leaves," maybe follows the plan, and perhaps later returns for follow-up. In the meantime, the user is presented with other simulated patients. To discourage cheating, the invention offers so many cases that a user observing another user recertify gains little advantage with regard to test content.

The system maintains records of the information gathered, the hypotheses entertained, and the recommendations made for each patient. After monitoring user performance on several similar cases, the program draws conclusions about the physician's ability to diagnose the particular class of problems. If successful performance is demonstrated, the class of problems are removed from further consideration for several years. Until successful performance has been demonstrated, the user receives feed-back on specific areas for improvement and continues to see cases from this class of problems.

Data structures that describe the activities of family physicians include a series of entity-relation diagrams, wherein entities represent things (nouns), and relations (verbs) illustrate how the entities interact. For instance, an entity-relation diagram of an address list might have an entity called "person," and an entity called "place," connected by a relation called "is at." The person entity would store people's names, the place entity would store addresses, and the "is at" relation would describe when and why this person is at that place. Thus, a person could now live at one place, previously live at another place, and continuously work at the first place. One person, two places, and three "is at" relations describe this address history. This address model is flexible and realistic.

The present invention further includes a mechanism for modifying relationships in the family medicine model, wherein inference programs within a relationship object determine what time-value series describe the relationship in context to a relevant query or Health State. The inference program may be implemented as a Bayesian Network. This dynamic modification of relationships provides a means of managing statistically dependent events in the context of co-morbid health problems.

The model employed in the present invention includes the major entities, relations and modifying relations shown in detail in FIG. 1. Formal concepts in the model are capitalized throughout the text. The model emphasizes diagnostic and management issues, variability in populations, and time. It describes consequences of anatomic and physiologic processes, but largely omits anatomic and physiologic reasoning as such. It is also capable of describing interpersonal relationships and may include an explicit representation of families or communities.

In accordance with the present invention, a plurality of major entities appear in the design: Patients, Records, Health States, Findings, Courses of Action, and Agents of Change. These entities and their relationships are discussed in detail herein below.

Records model beliefs about People. A Record's relations summarize inferences about a Patient. If a parent brings an infant to the office, this present invention represents the infant as a Patient, the parent as another Patient, and the parent's description of the infant as a Record. The physician can obtain historical information about the infant from two sources: the physician's medical Record of the infant, and the parent's Record of the infant. The physician can obtain current objective information by examining the infant as a Patient. The data linked to Patients are absolutely precise, but can be observed, if at all, only during medical encounters. Records summarize the history of those real data imprecisely and potentially inaccurately.

Patients have Records of themselves, modeling a patient's self-image and memories. As with other Records, a patient's self-Record summarizes historical information with variable accuracy and might be the physician's only source of some historical information.

A Patient is primarily a list of relations with other entities. A Record not only lists relations with other entities, but also defines encounters during which these relations were discovered. A Record can contain conflicting data acquired at different encounters.

Health States include all normal health states; classic disease presentations; early, subtle, or late disease presentations; and some disease combinations. Health States also include groups of Health States with shared characteristics, such as cardiovascular diseases and diseases of glucose intolerance. A number of commercial entities publish Disease Staging Clinical Criteria, defining numerous stages in the development of diseases.

Findings comprise genetic, physiologic, symptomatic, physical, and test-generated data, and clusters of such data. For instance, musculo-skeletal chest pain could be a Finding. This Finding could be an example of a Finding called chest pains, which would represent all kinds of chest pains. Chest pains could be an example of a still larger Finding called symptoms. Findings are defined by a collection of one or more Features, whose current value can be described by a number on a scale representing the value of a Feature. One Feature pertinent to pain is severity, which might be described on a 10-point scale.

Patterns describe the possible values of each Feature over time: a time-value series. A Pattern typically lists a series of values and corresponding percentiles at several points in time. Pediatric growth charts are the most widely used real example of Patterns. A blank growth chart illustrates at least the following observations: (1) Normal birth weights vary within a narrow range. (2) Weight increases relatively rapidly in the first few months and years. (3) The absolute variation in weight (e.g., the difference between the $90^{th}$ and $10^{th}$ percentile weights) increases after birth. (4) Most people reach a fairly constant weight by early adulthood. A pattern listing 10th and 90th percentile weights for people at age 0, 1 year, 2 years, and so on, illustrates the same concepts.

A growth chart may predict future values from past information. A child at the 50th percentile for weight now is expected to stay near the 50th percentile. If this child later reaches the $5^{th}$ percentile of weight, the expected pattern is absent. The ensuing diagnostic evaluation is an effort to account for the deviation by finding a weight Pattern that explains all observations. These concepts extend easily to many other physiological values, such as temperature. People have an average temperature of about 37° C., but some are a little cooler and some a little warmer. Normal temperature fluctuates within a narrow range during a lifetime, and most deviations from that range are considered abnormal.

Since many values change in predictable ways, Patterns might have cycles, sub-Patterns, and sub-sub-Patterns to describe these changes. The average value of a variable often changes during a lifetime, while the instantaneous value depends on a combination of annual, lunar, and circadian cycles. For instance, a nonpregnant 20-year-old woman should experience predictable lunar and circadian temperature fluctuations.

Sub-Patterns also describe consequences of other events, such as taking a drug. For instance, a dose of acetaminophen might lower a fever for 4 hours. A fever responsive to acetaminophen could be modeled by a high-temperature Pattern with a sub-Pattern indicating 4 hours of normal temperatures following acetaminophen doses. A person experiencing this fever and taking acetaminophen every 4 hours maintains a normal temperature. A physician observing this temperature Pattern would need to halt the acetaminophen to distinguish between a normal temperature and fever responsive to acetaminophen.

Sub-Patterns characterize Features and therefore Findings. For instance, one of the chest pain Findings might be "crushing substernal chest pain relieved by rest or nitroglycerin and exacerbated by exertion." This description implies a Finding with a designated location, a "crushing" Feature with some pattern, and 3 sub-Patterns describing the effect of rest, nitroglycerin, and exercise. The clinical appearance of simulated patients with this Finding might still vary, depending on the allowed variation in sub-patterns. For instance, pain might be more quickly relieved by nitroglycerin than rest or vice versa.

Finally, Patterns include small inference programs, such as Bayesian Networks, that maintain consistency between variables relevant to the simulated patient. For example, if a Patten describes "normal height" then the inference program may select a height growth curve appropriate for the sex and race of the simulated patient.

In Findings, the Specific Finding identifies a Feature with a Pattern that produces a percentile curve to represent the values of a Feature in an individual patient. For instance, although pediatric growth charts allow considerable variation in normal height and weight, one child will exhibit a precise series of values for both height and weight. Height will closely track one percentile curve, as will weight. The percentile of the height curve often limits the possible percentiles of the weight curve: healthy children at 95th percentile height rarely exhibit $5^{th}$ percentile weight. Most children follow a weight percentile equal to the height percentile ±20. The Pattern uses this equation to restate the familiar height-weight growth chart. Patterns model time and are one approach to interrelated medical observations. Time affects most numeric values in the model. Consequently, Patterns appear in nearly every entity and relation. Patterns describe the incidence of diseases at different ages, the likelihood of diseases progressing with time, and concentrations of drugs.

Courses of Action (COA) represent an activity undertaken that affects a simulated patient. Not only can these activities be medical, such as taking a blood pressure or performing a coronary artery bypass graft, but they can also include attending school, working, asking and answering questions, and following advice.

Patients invoke Courses of Action to decide when to visit a physician, how to answer questions, and whether to follow advice. Therefore, Courses of Action may advantageously be written to include missed appointments, lying to physicians, and ignoring physician advice. These actions could even depend on aspects of the physician's conduct, such as how the physician chooses to obtain information.

Query objects have complex internal structures, as will be discussed in more detail below. A query object corresponds to a question, a laboratory test, an imaging test, a functional test, or a diagnostic consultation. A query may belong to a larger group of queries related to a patient Health State. Query structures include a mechanism for collecting and processing data from at least one Health State, Specific Finding, or Specific Feature that is relevant to the query.

The data collected by a Query may be used to set the states of nodes in a Bayesian network, or may be suitably used as inputs to various other inference engines, such as fuzzy logic devices, neural nets, or rule-based inference programs.

Agents include physical, chemical, biological, behavioral, and social events capable of influencing Health States or Findings. These Agents can be therapeutic, injurious, or both. Agent descriptions include data about intake, metabolism, and excretion in the simulated patient, as applicable. For instance, a long-acting steroid is a chemical agent. Following intramuscular injection, the steroid will have predictable local and systemic concentration Patterns as the chemical dissipates from the injection site. The steroid might be metabolized to other compounds and excreted. Exposure to Agents normally occurs during a Course of Action, as this example illustrates.

The model of Agents describes their recognition, their presence, and the presence of metabolites or byproducts. Other parts of the model, such as the sub-Patterns of Findings, describe the effects of Agents.

Table 1 lists relations shown in FIG. 1. The Health States Lead to Health States relation describes how diseases evolve, and is therefore, critical for simulations. Preventive medicine scenarios might use this relation to generate patients who would benefit from screening. Case management problems can use this relation to model both the past and evolving history of a patient.

TABLE I

Relations Between Entities

Figure 8:
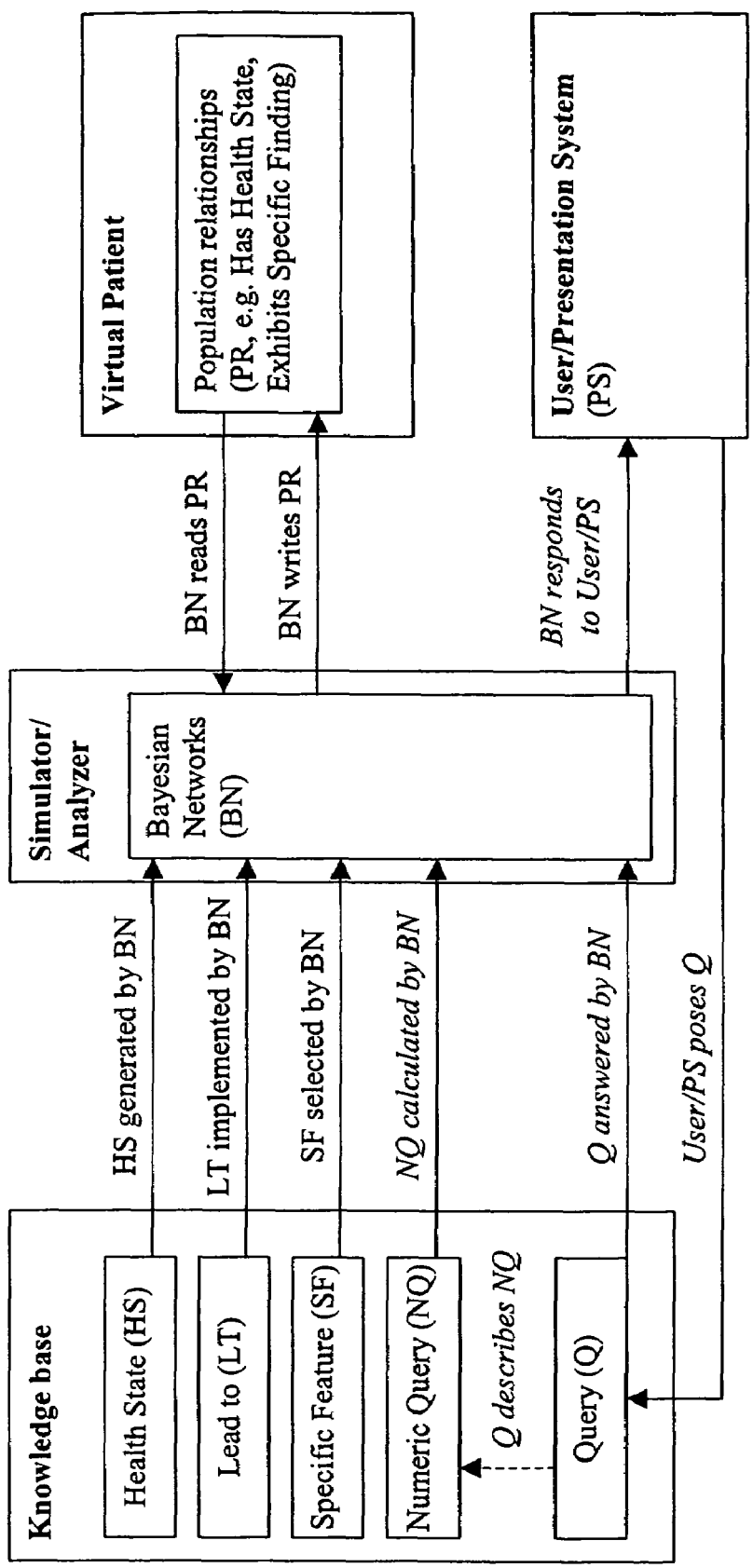
FIG. 8 is a block diagram of the interaction between the knowledge base, simulator, and presentation system in accordance with the present invention.

Patient Contacts Patient
Patient Related to Patient
Patient Interacts with Courses of Action
Patient Exposed to Agents of Change
Patient Has Health States
Agents of Change Cause Health States
Health States Lead to Health States
Findings Associated with Health States
Findings Link to Findings
Courses of Action use Agents of Change Furthermore, Table II lists the relations shown in FIG. 8 depicting the interaction of the Bayesian networks, used as inference programs in the present invention, and the virtual patient, the knowledge base, and the simulator.

TABLE II

Relations Involving Bayes Networks

Bayes Net reads Patient Relationships
Bayes Net controls Lead To implementation
Bayes Net generates Health State implementation
(generation method attribute)
Bayes Net selects Specific Finding →Specific
Feature→Time-Value Series
Bayes Net performs Numeric Query Calculation
Bayes Net assembles Query Response
Bayes Net writes Patient relationships The Findings Link to Findings relation describes causal associations between Finding Patterns, such as "severe cough causes abdominal muscle pain." This relation contains data about causality, mechanisms, and temporal constraints and facilitates reasoning about Findings.

The Patient Contacts Patient relation traces transmission of communicable Agents and potentially beliefs. Patient Is Related to Patient describes biological and social relations and the history of those relations, and traces transmission of genetic Agents. These two relations allow descriptions of arbitrarily defined families, with arbitrarily harmonious interactions.

The Patient Interacts with Courses of Action relation describes why the Patient began the Course of Action, what the Courses of Action cost interested parties, and how comfortable the Patient was during the Courses of Action. This model allows a patient to remember an unpleasant experience and resist having it repeated. Because Courses of Action can include negative (buying a therapy) or positive (receiving a paycheck) change in wealth, this relation is also capable of being used to model patients' economic inability to follow medical advice.

The Patient Exposed to Agents of Change relation describes perceptions about the exposure, knowledge of exposure, and the course of Action responsible for the exposure. This relation can describe exactly how an Agent was distributed in, metabolized by, and excreted from this Patient.

The Patient Has Health States relation includes the preceding Health State, a list of Findings attributable to the Health State, and the age at onset, diagnosis, and evolution of the Health State. Health States affect different individuals in different ways, and treatment often depends on the patient's impairments and perceptions. Consequently, a patient's beliefs about disease progression and perceptions of a Health States belong in the Has relation.

The Patient Exhibits Findings relation has similar perception attributes. Perceptions can be divided into Dysutility and concern. Dysutility indicates a trade-off a patient would accept to return to normal. Concern indicates a trade-off a patient would accept for full reassurance that a Finding or Health States does not portend future Dysutility. For instance, a patient with a minor left-sided chest pain might rate its current Dysutility as $5 ("I would spend $5 to relieve this pain for today."), and the concern as $100 ("I would spend $100 for assurance that nothing serious caused this pain."). If the pain persists unchanged, both of these values might decline as the patient learns to cope with the discomfort and becomes confident that the symptom has no prognostic importance. Thus, patients can have changing attitudes about stable conditions. Patients would typically seek medical care when provoked to so by a Dysutility or concern.

Records have the same relations as Patients, except that the details are always more ambiguous, inaccurate, or both. For instance, a patient might have influenza starting December 15, while his Record of himself indicates that he developed influenza between December 10 and December 13. The patient's Record of himself is both ambiguous (there are 4 possible days of onset) and incorrect (none of the days is December 15).

Furthermore, the data described in the Lead to relation often change with medical interventions or other events. For instance, an event might make evolution to another Health State more or less likely (regular low-dose aspirin reduces the risk of acute myocardial infarction), or could permanently alter the likelihood of exhibiting a finding (cardiac transplant prohibits myocardial ischemic pain).

Relationships of the form "Patient Interacts with Courses of Action" typically influence the Lead To relationships between Health States. For instance, appropriate management of an early stage of illness may slow progression to later stages of illness. In the model an inference program, such as a Bayesian network, mediates such effects by including Relational Conditions like Patient Interacts with Course of Action as input data. The input data influences the inference program's output. In the case of a Bayesian network controlling a Lead To relationship, the input Interacts with sets the state of an input node. The state of the input node affects the solution to the Bayesian network, and thus the state of its root node. The root node solution corresponds to a range of transition times. Although there is no direct relationship between Relational Conditions and Lead To relations in the model of the present invention, the latter does influence the former.

Two special classes of health conditions exist. First, normal health conditions are incident only at birth or conception, depending on testing goals. Second, "Alive" is a health condition whose prevalence shows the proportion of a cohort that survives to any age. The age specific prevalence and incidence of all other health conditions are defined as the percentage of living individuals at that age who experience or acquire the condition, respectively.

The Leads To relation connects one health condition (the precursor) to another (the target), and describes possible time intervals required for evolution from the precursor to the target. A Pattern describes a probability density function (pdf) of these time intervals, conditioned on comorbidities, treatments, and other risk factors. This duration pdf provides a time constraint mechanism. For instance, a duration pdf for the progression of mild to moderate knee osteoarthritis, given obesity, might indicate a probability density of zero in the first five years following the onset of mild osteoarthritis, a uniform probability density from year five to year twenty, and then a probability of zero. This implies that all simulated obese patients develop moderate osteoarthritis between five and twenty years after the onset of mild osteoarthritis, and forbids simulated onsets at other times.

Relational conditions referenced by the states of input Bayes nodes in the Bayes network of a Lead to relation also provide time constraints for risk factors. This allows the model to represent the concept that obesity must exist for a period of at least 10 and up to 40 years for this duration pdf to apply.

Finally, the Lead to relation provides information about how quickly and completely to convert from the findings typical of the precursor to findings typical of the target. For instance, if each knee osteoarthritis stage is a health condition, and each stage has a typical degree of joint space narrowing, then the transition from one stage to another should be accompanied by more narrowing of the joint space. The Lead to relation can indicate that this narrowing occurs over years, and that the narrowing is nearly complete when the simulation asserts that the latter osteoarthritis stage is present.

Referring now to FIG. 8, and in accordance with one embodiment of the invention the Bayesian Networks used as small inference programs are attributes of a plurality of entities in the system, defining a relationship between an object in the system and a virtual patient produced by the simulator. The Bayesian networks of the present invention may use continuous or discrete nodes, as required. Continuous nodes must acquire a numeric value. The states of the nodes define ranges of values, so that obtaining the value sets the state of the node. The states of discrete Bayesian nodes define categorical concepts, and in the current invention are either defined by relational conditions as discussed herein, or not defined at all. A node state is defined by a relational condition if the Bayesian node is an input node that reads from the simulator, or an output node that writes to the simulator. The node need not have state definitions if it represents an intermediate conclusion in the process of solving a Bayesian net, or supplied data other than relational conditions. A Bayesian network generates Health State characteristics for the simulated patient using the following method.

Initially, the knowledge base stores a description of Health States that is used to populate a plurality of nodes in the Bayesian network. Additionally, the aforementioned Patient relationships are used to define the node states of a plurality of nodes in the Bayesian network. The simulator reads these Patient relationships from the virtual patient to determine the states of nodes defined as inputs to the Bayes net. In the present invention continuously valued input nodes obtain a numeric value by inspecting the shape of a relational condition or Specific Features of a Specific Finding in an Exhibits relational condition. The states of a continuous node define a range of values, e.g. from 0 to 1, 1 to 5, etc. Discretely valued input nodes have states defined by the presence or absence of relational conditions.

The simulator next determines the value of any continuous nodes in the network's list of intermediate nodes. Continuously valued intermediate nodes calculate a numeric value from the continuous values already determined for at least one other Bayesian node. The continuous value of another node may serve as an input 'x' value in a graph, such that the intermediate node finds the corresponding 'y' value. The input values of one or more other nodes may be assigned to variables in an arbitrarily complex equation. For instance, and intermediate node formula may assign h=height.value where height is the name of an input node in the same Bayesian network. An intermediate node called 'mass' might have a formula bmi*(h*h), where bmi=body mass index.value and h=height.value. The Bayesian network is then evaluated to establish a state for all nodes in the network. Once this is accomplished the Bayes net writes new Patient relationships to the virtual patient by copying the conditions of defined output node states in the network. This process imbues the simulated patient with a Health State or States that exhibits Specific Findings, as shown in the entity relationship model of the present invention.

The Bayesian network process described herein above may also be used to implement the Leads To relationships that define the amount of time necessary to progress from one Health State to another. The Leads To objects link a Health State to its predecessor. Nodes in Bayesian networks may specify prior interventions or other risk factors necessary to transit from one state to another. The Leads To objects might indicate that a transition from, for example, glucose intolerance to type II diabetes takes 1 to 2 years in morbidly obese patients, 2 to 4 years in obese patients, and 5 to 10 years in normal weight patients. The Bayesian network is solved to determine the state of all Bayes nodes based on the Leads To inputs, and the new Patient relationships are provided to the simulated patient as detailed above.

Bayesian networks may also be used to represent a Feature of a Specific Finding. Subsequent to the Bayesian network being solved, the simulator looks for a specified root node of the network that is representative of a general physiological variable to select (stochastically) an associated time-value pair series representative of a Feature of a Specific Finding. All of the foregoing Bayesian network process may be initiated by the present invention responsive to the selection of a health problem or a plurality thereof to portray in a simulated patient. In a yet further embodiment of the present invention shown in FIG. 8, Bayesian networks are employed to provide answers to queries from users entered via a presentation system. This feature of the invention is further detailed below.

The data model described herein above is a highly structured and realistic representation of family medicine that guides the design of the knowledge base and supports the generation and evaluation of examinations. The following are strong assumptions: (1) Health States are discrete and distinguishable on the basis of associated Findings, which are also discrete and distinguishable on the basis of the Patterns of their Features. (2) After choosing a percentile curve in a Pattern to represent some value, the percentile does not change substantially. (3) Changes in Patterns (e.g., the probability of one Health State evolving to another) can be described for important combinations of risk factors, interventions, and time of occurrence. (4) Transitions from one Pattern to another can be estimated by simple means. (5) Modifying relations do not have important interactions with one another. (6) Highly developed anatomic and physiologic models are not necessary, because associations between Findings provide the same information.

Although the model should have places to store nearly all interesting facts about family medicine, test generation does not require a comprehensive description of all facts used in family medicine. The proposed test generates plausible problems from a set of data intentionally skewed to generate interesting (i.e., discriminating) cases. The present invention provides the flexibility to avoid controversial questions by controlling skewed data. For instance, if the management of borderline diabetes is controversial, the present invention allows editing of the family medicine knowledge base so that diabetics' fasting blood glucose levels are always markedly elevated. The family medicine knowledge base would then be incapable of creating a borderline diabetic.

Overview of Patient Generation/Evolution Processes

In accordance with a preferred embodiment of the present invention, a simulated patient is generated and presented as described herein below. The processes of the simulator are: Patient generation processes, including history outline processes and history generation processes; and Simulation processes, including presentation interface processes and Patient evolution processes.

Figure 4:
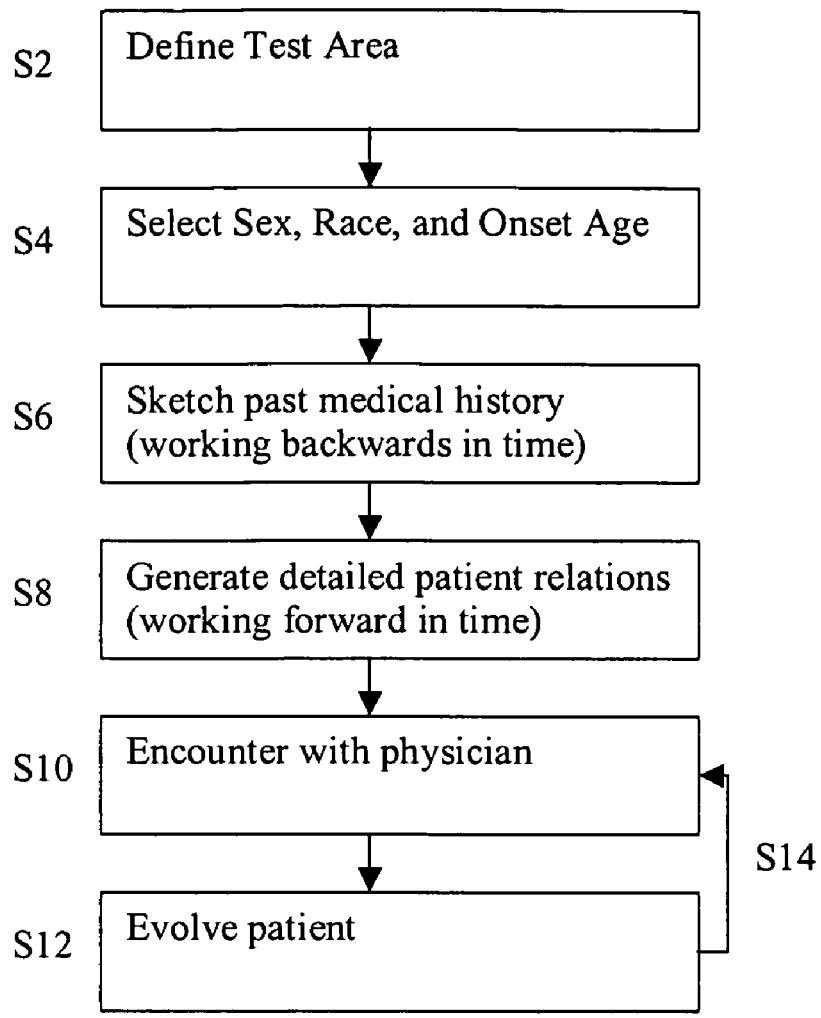
FIG. 4 is a flowchart of the overall process for the computer based examination system of the present invention.
Figure 5:
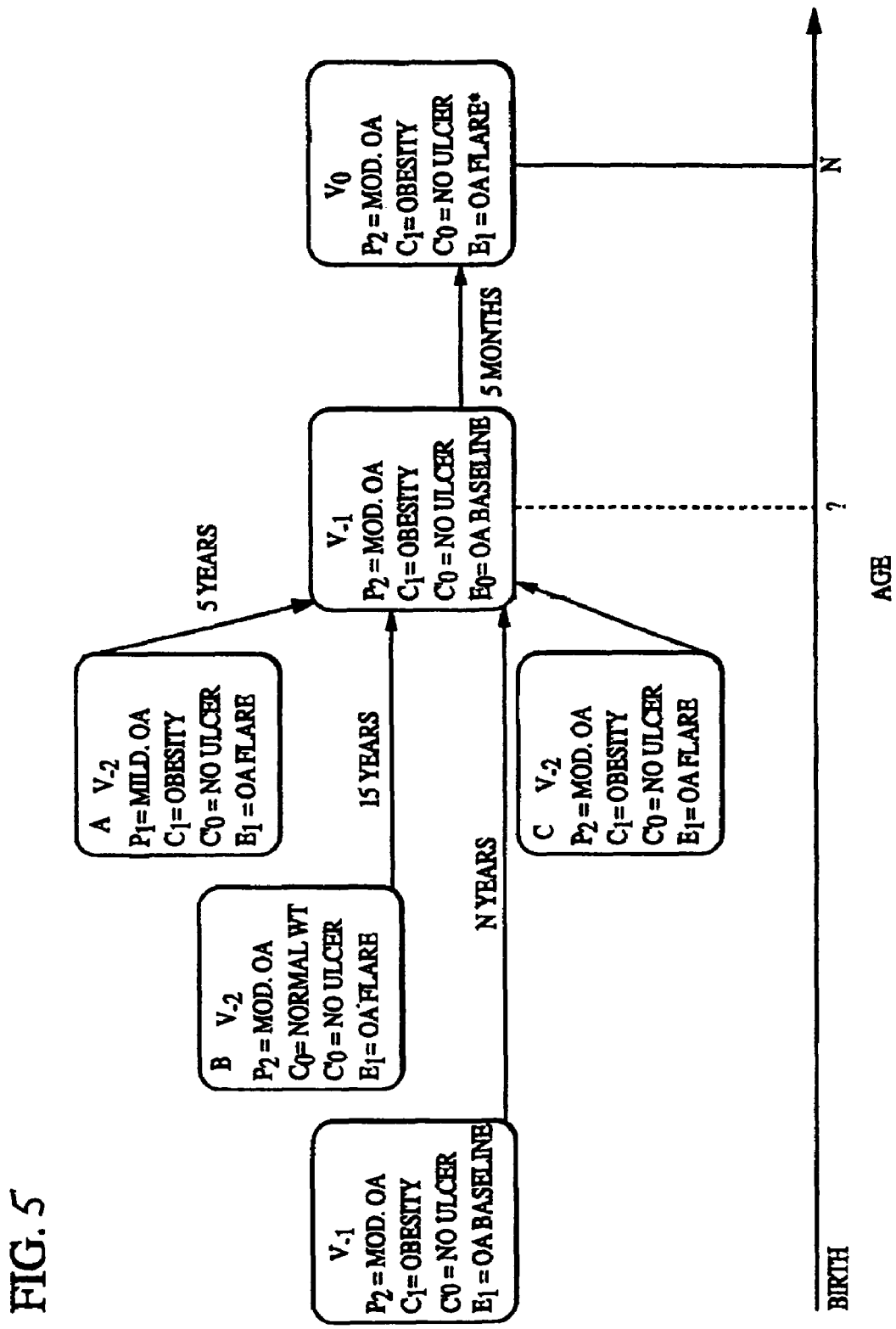
FIG. 5 is a flowchart illustrating a first step in tracing previous health conditions to generate past medical history of the patient for the stochastic process of the computer based examination system of the present invention.

Computer-implemented Patient generation processes are called once to produce a simulated patient for the examination session. Simulation processes may be called a plurality of times. The patient generation process presents the patient to the user, collect the user's responses and queries, and evolves the patient. FIG. 4 is an overall block diagram of the system of the present invention.

For the patient generation process, we assume that the area for the simulation—a specific object, say A, from the class AREA—and a health state, say H, from the primary network of the area A are given. For example, A may be the area of the adult onset diabetes and H may be the health state of symptomatic diabetes.

The patient generation process comprises two phases: history outline, and history generation.

The history outline phase generates a progression of health states and risk factors traversed by the patient on the way from a normal condition to the specified Health State H. It starts with a call to the procedure that establishes the sex, race and onset age (and therefore the overall age) of the patient being generated.

The simulator next selects the precursor state for the target state in the simulation as well as risk factors (circumstances) that will affect the patient. This will be accomplished by a call to the procedure OutlineFirstStep.

The next procedure, OutlineGeneralStep, is called iteratively until the normal health state is reached. In each iteration, it finds the precursor health state as well as its onset time. When a normal health state is reached, the history outline phase is complete.

The patient simulator next selects the last, first and middle names of the patient.

The OutlineFirstStep procedure generates the precursor state for the target health state for the simulation, and its onset age. In addition, it selects circumstances to which the simulated patient has been subject. This procedure also creates a History Element object containing the sequence of HAS for the precursors of TS, starting with the normal health sate and ending with TS. This sequence will be used later in the history generation phase.

The Generating history outline, and more specifically, the OutlineGeneralStep procedure, generates the complete path of precursors of the target health state. It starts in the normal health state and terminates in the target health state TS, representing each health state and transition (Lead To) by a different History Element (of course, the last but one state on the path has already been generated by OutlineFirstStep procedure).

Figure 6:
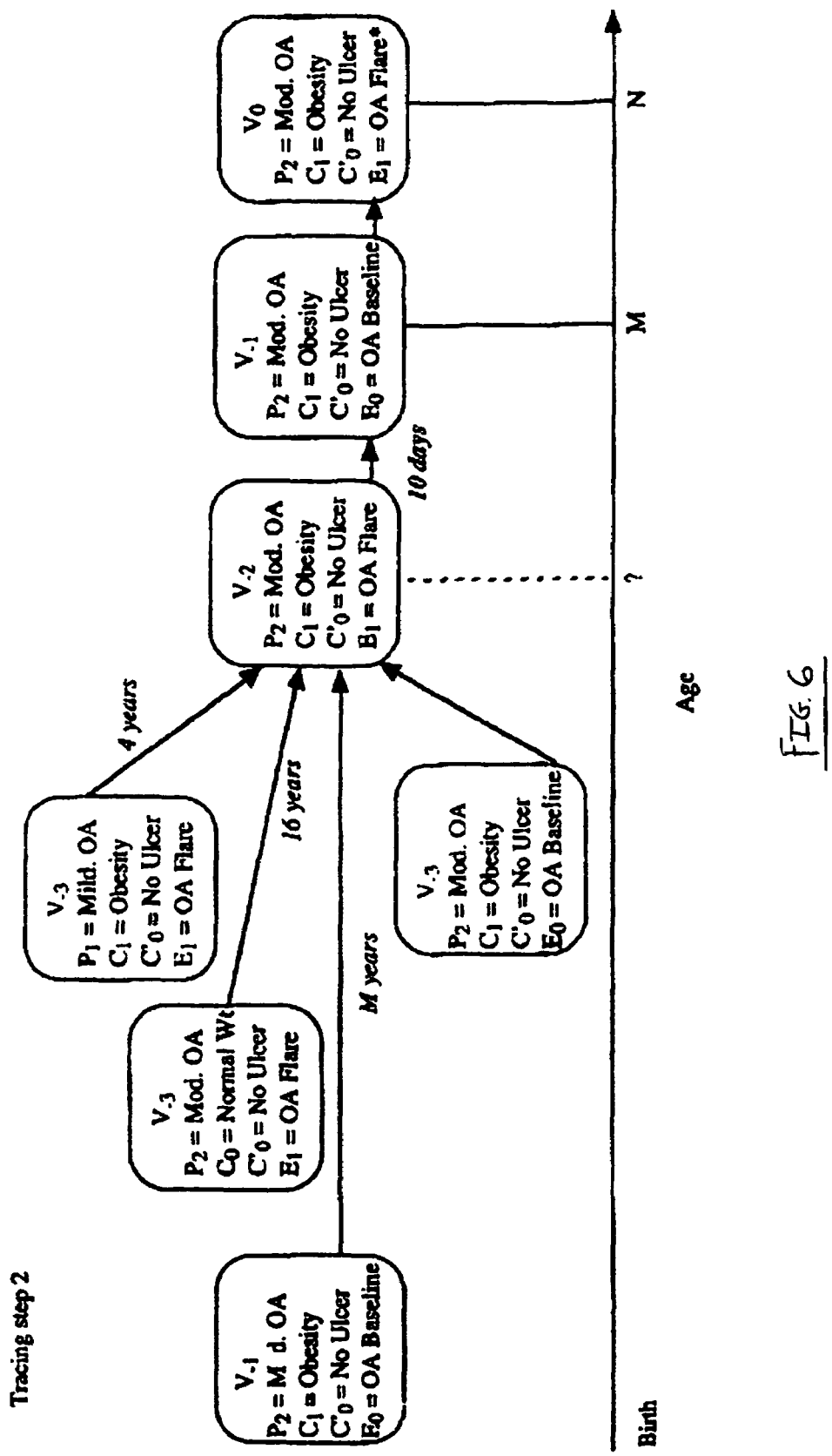
FIG. 6 is a flowchart illustrating a second step in tracing previous health conditions to generate past medical history of the patient for the stochastic process of the computer based examination system of the present invention.
Figure 7:
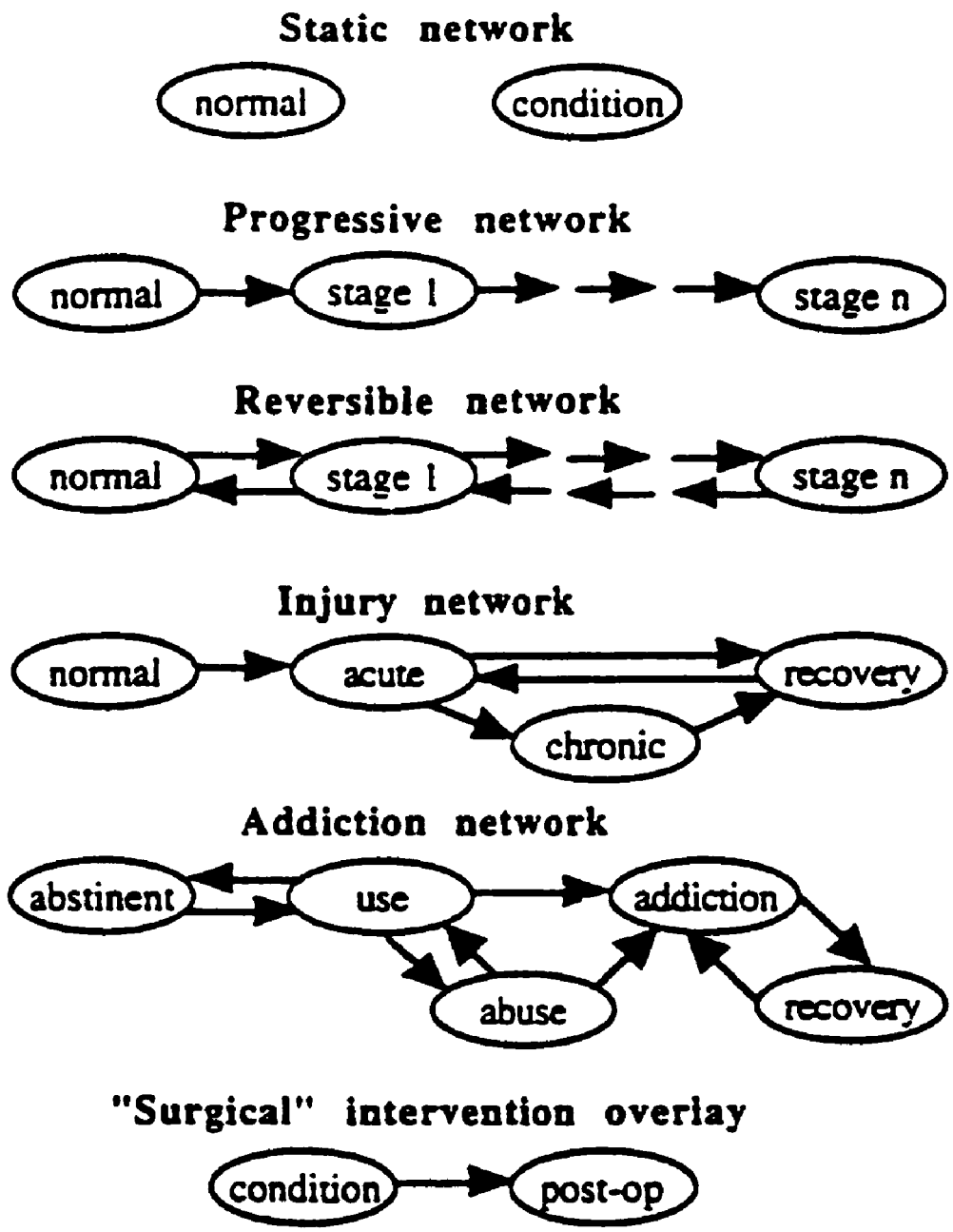
FIG. 7 is a flowchart depicting a plurality of parallel network types used to describe disease evolution in accordance with another embodiment of the computer based examination system of the present invention.

Referring now to FIG. 6, the history generation phase finds values that are established in each case when they differ from normal (normal values are derived from the defaults maintained in the knowledge base).

A Bayesian network, called a generation method, describes how a given health state or a risk factor determines a Finding. The generation method selects Exhibits Specific Finding relationships appropriate for the health state being portrayed. These relational conditions are copied to the simulated patient. The shape of each new relational condition is set to zero prior to the age of instantiation, and typically one thereafter, until the relational condition no longer pertains to the patient. The Specific Findings include Specific Features that provide detailed descriptions of time-value series representing baseline values and event-driven variations from baseline. Similarly relational conditions implied by each Lead To Bayes network solution are copied to the patient. The main input for this phase is the list of relational conditions already attached to the simulated patient.

The history generation process next looks at all associated objects and modifies values of patterns describing relevant relational conditions so that the detailed description of the patient is consistent with the health state history as created in the earlier phase. The invention inspects all History Elements, Health States represented by HAS instances, and sorts them according to their onset times. This results in a list in which all states normal in their areas precede all the abnormal states. The reason for this is that all normal states start at time 0. For each of these normal states the system will run its generation method, creating a list of Finding names and site names to which the Findings pertain, and defining the domain of all Findings for which specific descriptions are created.

Next, for every Finding, the patterns of its basic features are instantiated. These patterns are obtained from "normal" Specific Finding belonging to the Finding in question. To select specific curves, we use a percentile value. This value will generally be selected from the range uniformly at random.

After all normal states are processed, shapes for a plurality of relational conditions are instantiated. From now on, when generating other Health States these shapes are modified. The idea is to run the generation method for a Health State. As a result a list of sites and Specific Findings is obtained which must be modified. If only some sites for the Finding are generated, only those sites need to be modified.

The second major component of the simulation steps through History Elements to implement them in detail. The simulator sorts History Elements according to onset times, generally earliest first. For each History Element the procedure invokes the generation method Bayesian Network for each Health State, thus creating Exhibits tuples describing Findings associated with Health States, and other relational conditions as specified. The shapes of relational conditions generally indicate whether the object of the condition, such as a Health State or Specific Finding, is present (1) or not (0) at a given age. The shape of an Interacts With Course of Action relational condition represents the dose of the intervention at any given age. The shape of a Calculated Numeric Query relational condition indicates the value calculated at certain ages.

The present invention generates a large number of plausible medical history outlines. It automates the authoring of major events in the lives of simulated patients by applying a Monte Carlo process to multiple stochastic trees, to generate large numbers of plausible case outlines. Further automation of these outlines yields complete, usable simulated case histories.

The present invention utilizes a plurality of parallel Health State networks. A given Health State network is "parallel" to many other networks of Health States that exist simultaneously in a person. In general, a parallel Health State network lists transitions that occur among an exhaustive set of mutually exclusive Health States occurring in one body part. For instance, the left knee of a patient exists in one of the Health States in the osteoarthritis network. The right knee also exists in one of these states, but not necessarily the same state found in the left knee. The patient simultaneously exists with one state in a gastric ulcer network, a weight network, and numerous other networks.

A simulated patient's overall medical condition is therefore a vector, V, listing the current health condition from each parallel network at each involved site. A case specifies vector $V_0$, indicating the health conditions instantiated at the initial presentation of a simulated patient, and sufficient information to create a history of vectors culminating in $V_0$.

A plurality of the parallel networks in any given case are inactive. These define an initial, usually normal, (stage 0) condition of the parallel network. Most cases contain a few active parallel networks. Active networks presenting at stage 1 or higher represent active medical problems. Active networks presenting at stage 0 represent potential problems, such as complications resulting from an active problem or its treatment. The user's task is generally to identify and respond to active networks in advanced stages, while minimizing disease progression in active networks at stage 0.

Active networks may be described as primary or comorbid. Primary networks typically represent the main testing topic. Comorbid networks may represent typical concurrent conditions, distractors, or atypical concurrent conditions with important implications for evaluation and management. For instance, osteoarthritis could be a primary network accompanied by comorbid networks for obesity, urethritis, and gastric ulcer. Obesity is a typical comorbidity, urethritis is a distractor suggesting Reiter's syndrome, and gastric ulcer has implications for analgesic selection.

When an active parallel network describes a chronic condition, acute exacerbations may be expected with some of the health conditions in the network. An exacerbation network "E" is a parallel network describing acute flares of illness that occur during a more chronic health condition. For instance, flares of knee pain with effusions may occur in patients with chronic osteoarthritis. In principle, health conditions within an exacerbation network can have their own exacerbations. The simulation process of the present invention allows exacerbation networks to contain cycles, unlike primary and comorbid networks.

A simulated patient's medical history is the sum of the events culminating in the case defining vector, $V_0$. The case provides sufficient information to create many plausible histories, but does not store histories. Consider a case defined to culminate in severe bilateral knee osteoarthritis and morbid obesity. The relative sequence of events on the primary and comorbid networks are not necessarily constrained. Obesity might be required to occur before the onset of mild osteoarthritis. However, the onset of morbid obesity could occur before or after the onset of moderate osteoarthritis.

Evolution can be assumed to occur along only one parallel network at a time. If evolution in two networks can occur simultaneously in life, one can be assumed to occur first, and the other a moment later for purposes of the model.

Parallel network evolution may interact in three ways. First, the networks may be completely independent so that evolution along one has no implications for another. Secondly, progression through one network may depend on the concurrent condition of an independent network. For instance, the incidence of early osteoarthritis conditions could depend on the concurrent condition of the other network. For instance, a realistic simulation of a severe osteoarthritis history might require modeling a "vicious cycle" where obesity accelerates osteoarthritis, which in turn accelerates obesity. Virtuous cycles" are also possible, in which improvement in each network accelerate improvements in the other.

The age of onset of the Health State previous to any Health State in V is constrained by the age specific incidence of the previous Health State and the speed of transitions permitted between stages. Incidence of Health States is defined by Bayesian networks linked to Health States. Transition times are defined by Lead To objects that link preceding and succeeding Health States. An age-sex-race specific incidence of the previous Health State can be multiplied by the probability of a transition occurring at the corresponding time. For instance, if a simulated white female patient developed a health problem at age 40 years, and the incidence of the preceding state in white females at age 35 is 0.1%, and the probability of transition from the preceding state to the current state in 5 years is 15%, then an appropriate weight for selecting a transition at age 35 is 0.001×0.15=0.00015, or 0.015%. The simulator will calculate similar weights for onset of the preceding state at other ages, such as 34 and 36 years. The simulator uses the weights to stochastically select the age of onset of the preceding state. A series of similar operations allows the simulator to construct a past medical history in multiple steps.

The present invention further provides for automated generation for Finding Objects. Finding generation adds detailed descriptions of patients' features to the outline generated in the steps above. Beginning with a healthy newborn patient (or embryo) of the specified sex and race, the Finding generation process assigns values of Specific Findings expected in healthy individuals. These may change when the patient develops a new health state at the age selected by the outlining process.

The patient's detailed features are generated using modeling instructions stored in Bayesian networks with health states. Specific Findings associated with normal health are created in a sequence indicated by these instructions. Each Specific Finding is initially defined from the onset of life until age 100. For instance, the patient's height is derived from a randomly generated percentile and a set of shapes resembling a pediatric growth chart extended to age 100. The set of shapes used may be conditionally dependent on the sex, race, and any other established facts about the patient.

The Finding generation process should generally create dependent Findings, e.g., knee pain, after generating the Findings upon which they depend, e.g. joint space narrowing. Careful selection of Findings to represent may reduce some dependencies. For example, the model in general is more robust if height and body mass index are considered to be independent Findings, and weight is not calculated until explicitly requested during a simulation. Therefore, the model in general is more robust if height and body mass index are considered to be independent Findings, and weight is not calculated until explicitly requested during a simulation. Most Findings are instantiated as a series of pair of values and ages. Values at other ages may be found by linear interpolation.

Findings may vary with predictable circadian, lunar, and annual rhythms, described by shape subpatterns. Shape subpatterns can be combined with a shape to produce fluctuations on realistic temporal scales.

Finding distortions illustrate events having temporary effects on the shape of some value. For instance, a temperature shape during a febrile illness might be 39° C., with a distortion pattern indicating a 1° C. drop for four hours following administration of acetaminophen. The exact temperature reported at a given time would depend on the current value of the lifetime temperature shape and whether the patient consumed acetaminophen in the last four hours.

After determining patterns for all findings present at a point in time, the simulator proceeds forward in time to the next health state vector. The simulator updates findings for the new health situation. This iteration of steps continues until the computer has described the findings of the patient in the final health state vector.

There are two basic actors in the computer implemented examination system: physician, and patient generator (simulator). The user initiates the administrative database action by logging in. Once the user logs in, then the administrative database makes one or more requests to the patient generator. The administrative database generally provides the patient simulator with the basic testing area. The patient generator then starts the process of generating the patient, or "cloning" a pre-generated patient. Thus, the computer based examination system includes separate programming objects in the general C++ programming sense for physician, the patient and the administrative database.

In general, the user pre-registers to take the examination, and provides (or the system already has stored) detailed background information on the physician, areas of weaknesses, prior examination information, and the like. Thus, the physician logs-in to the computer based examination system and the system validates the physician in accordance with predetermined criteria, e.g., user ID, password, correct examination, and the like.

The user is either presented with an optional list(s) of subject areas for examination or mandatory subject areas for examination in, responsive to information stored in the administrative database via requests thereto. Alternatively, the examination areas might be hidden, and the user might be told that this is a diabetic problem, with certain management issues. The user may optionally have a series of selections, whether it is in terms of individual patients or they could be in specific areas.

The parallel Health States are also used to establish the Findings, which contribute to the patient history. While the above steps have been described in, more or less, a sequential manner, it should be clear that the various steps described herein may be performed in parallel, independently, and/or non-sequentially, as needed or for computational efficiency.

Computer-Implemented Patient Interaction

The present invention is further capable of the development of temporal events in a simulated patient such that a diagnosing physician may inspect the duration of events that impinge on the simulated patient's health and be presented with temporally reasonable reports. The patient simulator of the present invention can construct and present patient symptom histories that are both physiologically and temporally reasonable given the patient's Health State and any interventions or courses of action that may have been prescribed by a diagnostician. Furthermore, the invention provides a method for modeling concurrent diseases in the same patient by distinguishing Findings or patient symptoms that may be identical or substantially similar for the concurrent diseases, even where they have dissimilar biological causes and require dissimilar treatment from the treating physician.

The method of patient simulation is capable of interacting with a user such that the simulated patient communicates the presence of pain (a site), and the palliative, provocative, quality, radiation, severity and temporal details thereof. These details are commonly known as the PQRST symptom details. Thus the invention generates a simulated patient that include the presence or absence of a health problem, any Findings related thereto, and the existence and effects of any interventions, prescribed or otherwise, over time. The patient simulator may further inspect these details and produce reports to the user that are temporally reasonable given the patient's history.

Furthermore, where the user's query requires the simulated patient to summarize the overall results descriptive of the typical characteristics of multiple events such as angina attacks, the system and method of the present invention produces a complete response that may include multiple parts, which may not be logically possible when taken separately. For example, in response to a query regarding angina over time, a patient may respond thusly: "Rest completely relieves my pain in about 20 minutes. Nitroglycerin completely relieves my pain in a few minutes, but not if I continue to exercise." This response includes details about the patient's level of relief and how quickly it occurs under certain circumstances. Additionally, in order for the response to present a complete picture of the patient's pain, several details must be appended together.

Accordingly, one object of the present invention is a system and method for generating a simulated patient responsive to a user query regarding health symptoms that includes details on palliative, provocative, qualitative, radiation, and temporal factors of the patient, and producing a response that is reasonable both temporally and physiologically.

In one embodiment of the present invention, the simulated patient may report to an examining physician a plurality of physiologically and temporally reasonable symptom histories when queried. The simulation process of the invention can model diseases concurrently by distinguishing, for example, findings of fatigue in a patient that may emanate from more than one disease. Furthermore, the simulator distinguishes the implications of interventions or treatment for the diseases. As one example, fatigue caused by hypothyroidism is alleviated with thyroid replacement, but is unaffected by serotonin reuptake inhibitors that may be prescribed to address fatigue resulting from clinical depression.

Figure 9:
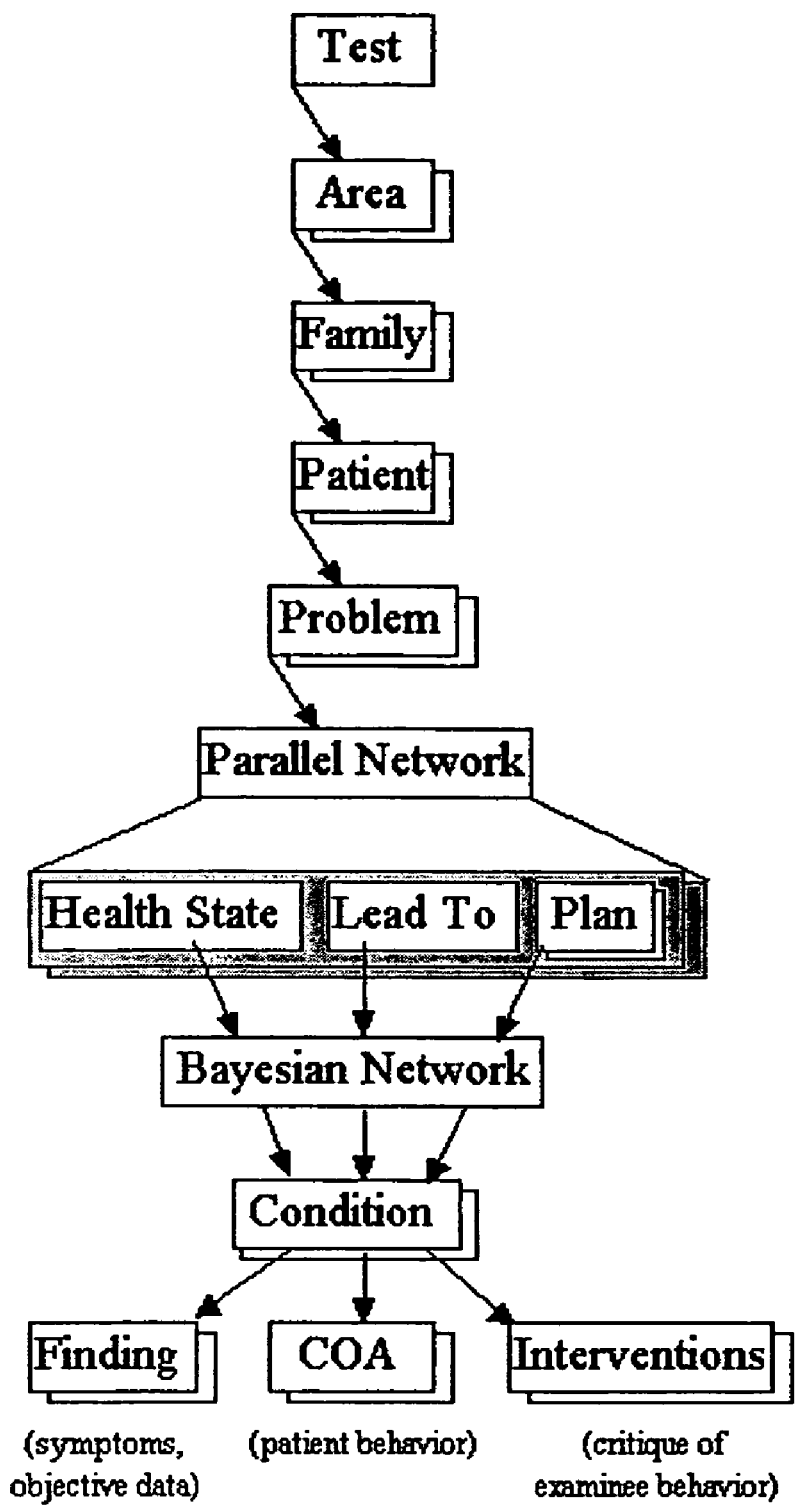
FIG. 9 is a block diagram of knowledge base organization in accordance with one embodiment of the present invention.
Figure 10:
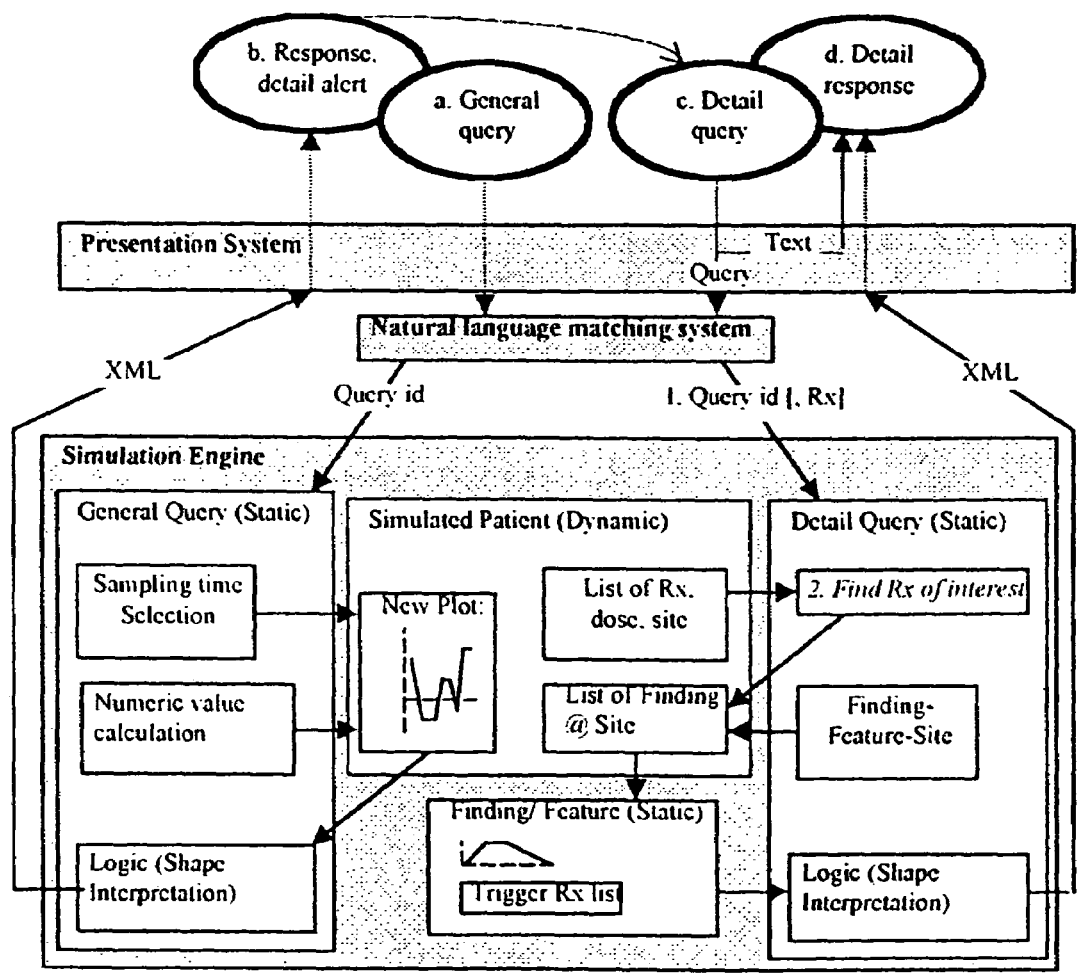
FIG. 10 is a block diagram of a query process in accordance with one embodiment of the present invention.

As best seen in FIGS. 8, 9, and 10 the present invention employs a process for producing temporally and physiologically reasonable symptom histories in a simulated patient by first accepting a general query from a system user that is used to establish a plurality of time points that are relevant to the query, calculating a symptom status value at each of the time points, and then evaluating a plot of the symptom status values versus time to determine a general description of the symptom history for the simulated patient. This general description is then reported back to the user (physician) utilizing a report template.

In the initial step in this process a user provides a query to the simulator requesting general symptom information from the simulated patient. The presentation system parses the general query to determine the context of the query using a language matching program, and identifies the requested query to the simulator. The simulator then accesses the knowledge base wherein a list of sampling time points are stored for the Query, expressed as offsets from the present time. As an example, if the sampling times in the list are 0, 0.1, 1, and 2, and the current age of the simulated patient is 40, the ages to sample are 40, 39.9, 38.9, and 36.9 respectively. The simulator then searches for all prior data related to the context of the query for the simulated patient.

As one example, a query that relates to a patient's fatigue or tiredness may employ a Numeric Query object to generate data regarding the symptom concept called "energy level". For each symptom concept, a simulated patient supplies a plot of the previously calculated status of that symptom over time. The simulator then accesses this plot and compares the list of time points with the symptom points already plotted. Points in the plot that are proximate previously established points are discarded. For points that are not proximate existing points, the simulator plots the symptom status at that time (patient age).

The second step in the process is to utilize a Bayesian network attribute of the Numeric Query to calculate a symptom status value at each of the time points. As best seen in FIGS. 1 and 8, the system next examines Findings that are relevant to the user supplied query and the effects of any interventions prescribed by the user thereon to calculate an overall symptom score at a specified temporal point. A user intervention can include prescriptions of medications, which typically comprise information on both dosage and frequency of use for a patient. The system can accept a prescription and interpret it to mean that at a specific patient age, for example 34.1234 years, the patient consumed a specific dosage of medicine, for example 50 mg of levothyroxine.

A Specific Finding object, through its component Specific Features, comprises a baseline value of a physiological variable and information regarding the effects of certain perturbations to that variable over time, including a plurality of curves or plots that describe the action of doses of medications that trigger responses in the value of the Finding. A user-supplied intervention may trigger a plurality of dose-response curves since the intervention may have an effect on a plurality of physiological variables over time. The Bayesian network comprises a plurality of nodes for baseline values of physiological variables, the effect of a plurality of interventions (medications) thereon, the net contribution of all interventions on the relevant variable, and a calculated overall variable status value. Many of the Bayes nodes in this network are continuous. Input continuous Bayes nodes obtain raw data from the simulated patient's relational condition shapes or the time-value series contained in specific features of Specific Findings in Exhibits relational conditions. Intermediate continuous nodes may use equations to calculate their values from these raw data, previously calculated values, or both. Intermediate continuous nodes may also map one value to another, using another nodes' continuous value as an 'x' value, and finding a corresponding 'y' value in an x-y plot. Some nodes will utilize the raw data as baseline Finding values, while others will obtain the response of the physiological variable to the recent interventions.

When the simulator reaches such a node, it performs several checks to ensure consistency between queries. Initially, the simulator determines the window of time covered by a single dose of the prescribed intervention, i.e., how long the intervention would affect the patient, then inspects the patient to determine whether a relevant intervention actually occurred during this time period. If the intervention did occur during this time period, the simulator calculates the patient's age at any missing dosing events during that time period and provides the missing dose at that age. The simulator then makes these doses a permanent part of the simulated patient, which may be used responsive to subsequent queries.

The simulator next constructs a dose-response curve to approximate the patient's response to the dose prescribed in the intervention. The simulator may, where necessary, interpolate between a pair of dose-response curves where the response to the dose given is not readily available. For example, in the case of a 50 microgram dose of a given medication, the simulator may interpolate between dose response curves for a 20 microgram dose and a 200 microgram dose to determine the proper response. The simulator then utilizes this newly interpolated response data to calculate the contribution of each dose taken during the time period being investigated. This method of producing dose-response curves and a patient's response over time to an intervention serve as a colorable approximation to the effect of a dosage of drugs on a patient.

Once the dose-response curve is generated the simulator solves the Bayesian network to establish the state and value of a node in the network that specifies an overall symptom score or value at the time specified time (a root node). The solution to the network may be stochastic, employing Bayes' theorem, or purely numeric, employing only closed calculations organized by any convenient mechanism, including Bayesian networks comprised only of continuous Bayes nodes. The simulator would then include the resultant time-value pair to the plot of symptom status versus time. The simulator can then look at the symptom plot over the time period included in the query in order to provide a reasonable answer to the user regarding the symptom status.

A report-generating Bayesian network then utilizes a plurality of symptom plot parameters to generate a report to display to the user via the presentation system. A plurality of Bayes nodes collect symptom parameters such as duration, average value, number of slope sign changes, time spent below zero, or slope of a best-fit approximation or linear regression. The evaluation of this reusable network can produce a report that includes the symptom's frequency of fluctuation, severity, and a general trend over the queried interval. For example, a report on fatigue could be "I have been tired most of the time for the past few years. I am improving a little." The average value of the symptom plot causes the Bayes network to select the phrase "tired" while similarly duration selects "the past few years", time spent below zero produces "most of the time" and a regression slope selects "improving a little".

Based on the foregoing, the system and method of the instant invention produces a simulated patient and a response to a query regarding general symptom status supplied by a user that is both physiologically and temporally reasonable given the patient's health status. This feature of the present invention permits a system and method that is capable of modeling the symptoms of a simulated patient as responses to general user queries, rather than as a collection of symptoms that must be generated in advance for each simulated patient.

In accordance with an additional embodiment of the instant invention, a system and method is provided for generating a simulated patient that is capable of relaying PQRST details to a user responsive to a user supplied query and/or a user intervention. Referring again to FIGS. 1, 8, 9 and 10, a computer implemented process for generating a simulated patient and symptom details relevant thereto comprises the steps of using the presentation system to identify potential details of interest responsive to a user supplied general query, identifying prior interventions (and the patient's response thereto) that are of interest based on a detailed query, identifying Findings and Features in the knowledge base that are relevant to the detailed query, identifying any effects that may be triggered by an intervention prescribed by the user physician, and finally generating a detailed response report utilizing a Bayesian network, as previously detailed herein above.

Initially, a user physician may supply a general query regarding patient symptoms to the present invention using the presentation system. The presentation system then utilizes a natural language matching system to match the topic of the general query with a query object in the simulator most closely associated with that topic. A plurality of commercially available natural language matching programs may be employed to accomplish this task, for example Kiwilogic or the ALICE artificial intelligence bot. In an alternative embodiment of the invention, the presentation system may employ dialog boxes, pull down menus, or topics lists and details related thereto that may be selected by the user via mouse or other operator interface of the presentation system to indicate their query topics and the details related thereto.

Initially, when a user types (or otherwise submits) a general query using the presentation system, the matching system conducts a search to locate a Query object in the simulator that is most relevant to the Query topic. An exemplary Query object in the present system comprises the following attributes:

```
Query Object
    Sampling List [Time Point]
        Value Calculation [Numeric calculation of
symptom value]
        Shape Source [Finding/Feature/Site]
        Logic [Bayesian Network]
            Root Node [Bayesian Node]
                State List [Node State]
        Report Template [Text Formula]
        Detail List
            Detail Type [PQRST list]
            Root Node State [Node State]
            Report Template [Text Formula]
            Query [Query]
```

A Query object may represent an abstraction of other Query objects. For instance, a Query object representing the question, "Do you have any pain?" may be an abstraction of queries that represent more specific questions, such as "Do you have a headache?" and "Do you have knee pain?" The specific Queries are descendants or children of the abstract Query. A patient portraying a particular Health State may be likely to give an abnormal response to a specific Query that is a child of an abstract Query. In one embodiment of the invention, Patients may maintain a list of specific Queries that are likely to yield interesting results, and use these exclusively when the user selects the Abstract parent of said specific Queries. This does not prohibit the user from directly asking any other specific Query, including other children of the abstract Query.

The simulator of the present invention generates a response to the general Query by initially determining whether to use a Numeric Query. If the Query includes a non-null Numeric Query attribute, the simulator examines the sampling list of time points and corresponding values for those points that are representative of the relevant health detail of interest, and calculates any missing values. The logic Bayesian network is next solved to determine the node states, including the state of the root node of the network, which is typically used to provide a general summary of the health detail that is the subject of the query, often whether that symptom is present or absent in the simulated patient. As an example, in the case where the Query object relates to chest pain, the root node may include two states: chest pain present, or chest pain absent.

The simulator next assembles a report using the object's report template. The report template typically comprises a text string having a plurality of node references embedded therein whereby the node references may be replaced by text that is associated with node states depending upon the matching procedure discussed in more detail below. This report is eventually presented to the user via the presentation system. In a preferred embodiment of the present invention, the report is advantageously generated as an XML document. This report format is particularly effective for allowing for a plurality of embedded reference tags to be inserted in the report, wherein the simulator retrieves the necessary information to populate the embedded reference tags.

The Query object detail list shown herein above may comprise a plurality of symptom details relevant to the symptom of the Query, each of said details containing zero or one states of the root node of the Bayesian network representing the Query's logic. The simulator next examines each of the symptom details in the list to determine whether the detail root node state matches the previously determined root node state of the Query object logic. If the detail does not identify a root node state, it matches all root node states. That is to say, if no root node state is available for a particular detail (i.e. the root node is a null value) the system determines that particular detail to be of relevance to the Query. Any non-empty subset of these details that are matched to the root node state using the process described above, will include details with one or more distinct types in the PQRST categories. This subset could have multiple details within the same type. For each unique type (PQRST) in the subset, the simulator adds a set of <Detail> tags to the XML report in preparation to receive the detail report template.

If the report template for the detail is not empty (in certain cases a detail's report template may point to a reveal or other object to obtain its contents), the simulator uses the original Query object's Bayes net to insert phrases replacing the relevant node references in the template with associated text that describes the palliative, provocative, qualitative, radiation, severity and temporal aspects of the detail being reported. Once populated with the requisite text, the simulator places the template between the <Detail> tags, and inserts a text marker.

Where the detail report template is empty, the detail itself contains a tag that identifies a Query object relevant to that detail. This feature of the instant invention is particularly useful where responses are required to temporal queries such as "When does your pain abate?". Such detail queries may require distinct data, not described in the Bayes net representing the logic of the original Query. Therefore, the knowledge base may represent any detail that requires a separate analysis of patient data as a distinct Query, to evaluate just as the initial Query was evaluated. In one embodiment of the invention the detail Query can itself have further sub-details.

The XML report produced by the simulator is then sent to the presentation system and presented to the user as a response to the original query. In a yet further embodiment of the present invention, available details in the response may be presented to the user as hyperlinks or list boxes, pull down menus with selectable details, or any other suitable system whereby a user can select the detail for further investigation. Additionally, a user may further search for details using a natural language query as described above. A query about a detail returned in the report could immediately be identified and the detail information, including any PQRST details related thereto and intervention effects are returned as a result to the user.

The simulator next identifies any interventions that may be relevant to a detail Query. When information about a specific intervention is requested from the user, either through a natural language query, or using a check box or hyperlink, the simulator examines any interventions in the simulated patient's medical history to determine whether any of these are common to the specific queried intervention. If none are found within the time frame specified by the Query, then a negative response is provided to the user through the presentation system. When the user does not identify any specific interventions, all current medications are considered potentially relevant interventions.

Once the relevant interventions are identified by the simulator, a user's detail query is examined to locate a Query object in the simulator that most closely matches the topic of the detail query. The Query object located responsive to the detail query may have an object structure identical to the Query object discussed herein above. Alternatively, the Query object may further comprise a shape source attribute that contains data relating to a Finding, Feature, and Site that may then inspected by the query matching system to locate a Finding, or a plurality thereof, that is pertinent to the user's detail query. A Finding is an object containing physiological data relevant to and descriptive of the simulated patient. An exemplary Finding object structure is set forth below:

```
Finding
    Specific Finding List
        Specific Feature List
            Feature
            Pattern List
                Trigger
                    Intervention
                    Dose
                    Time-Value Series
```

A Finding may be divided into a plurality of Specific Findings that contain information regarding diagnoses relevant to the underlying physiological data of the Finding. For example, a Finding may describe myocardial oxygen supply parameters while a related Specific Finding may correspond to varying stages of coronary artery disease. The Specific Findings comprise a list of Specific Features each of which in turn is comprised of a Feature and Pattern List related thereto. The Patterns are typically interventions that trigger some physiological response for that Feature as well as a dose for that intervention, and a plurality of time-value pairs representative of a value of that feature's response to the dose over time.

The intervention supplied by the user above (if any) is next compared to the list of trigger interventions located in the previous step to determine if any time-value pair series related to the prescribed intervention exist in the simulator. If the relevant prior intervention time-value pairs are located, the simulator will compare the dose prescribed with the intervention to the dose administered in the time-value series, and interpolate, if necessary, to calculate a simulated response for the simulated patient's relevant feature to the prescribed intervention. This calculated response is also in the form of a time-value pair series.

Where the simulated patient has no relevant trigger interventions to be located, (i.e. the simulated patient does not use an intervention) the simulator then determines whether the patient used the intervention in the time period that was the subject of the general query. Typically, a general query will span a time period of several months, since the user physician often inquires about the status of a symptom or symptoms over the past few months. If an intervention has any overlap in time with the simulated patient's symptom or symptoms, the simulator additionally obtains the time-value pairs associated with that intervention so that it can be presented to the user, as described in greater detail herein below. This feature of the present invention permits the system to understand that interventions, related to a user query or otherwise, that transpire during the time period of the general query are presumed to be relevant to the patient's symptoms, and thus to the user's query.

Once the simulator has compiled a set of relevant interventions for the simulated patient, and the corresponding Findings, Features, and time-value pairs associated with the interventions, a detailed report is generated, preferably as an XML document, that describes the simulated patient's symptom status in detail. As disclosed above with respect to report generation corresponding to a general query, a Bayesian network having a plurality of predefined analysis nodes is provided the time-value series as an input thereto. The analysis nodes may describe a plurality of parameters inherent in a plot of the time-value pair series, including but not limited to duration, the times corresponding to the maximum and minimum values, the slope of a best-fit line approximation, the number of slope sign changes, etc. This Bayesian network can further access other descriptive information (as input data for node states) resident in the simulator, such as the presence or absence of specific diseases or interventions. Once the node states of the network are populated with the aforementioned input data, the Bayesian network is evaluated. The node states in the network solution are then associated with text strings as previously discussed, thence appended to an XML document and presented to the user as a detail report on the patient's symptom status.

As can be readily seen by one of ordinary skill in the art, the resultant report may include details of the simulated patient's symptoms that include palliative aspects that may or may not be related to interventions, provocative events, radiation and qualitative aspects of pain all set forth in a reasonable temporal context. Furthermore, the system and method of the present invention can readily perform the process described above for each intervention and detail Query object located by the simulator as relevant to the detail query, and solve the Bayesian network to evaluate each intervention's time-value series. Thus the detail report generated can contain the aforementioned details pertaining to a plurality of symptoms and interventions in a single simulated patient.

In accordance with another embodiment of the present invention, an interval history method facilitates testing of users unfamiliar with computer interfaces by minimizing the number of times that the user must locate questions, whether by pointing, typing, or speaking. Furthermore, this embodiment of the invention facilitates the generation of natural descriptions of patient symptoms that might change between visits due to helpful or harmful interventions or changes in disease stage and facilitate the generation of patient symptoms that develop responsive to an intervention, especially including unintended side effects of the intervention. Additionally, interval history generation methods do not significantly compromise the testing function of a simulation program because a) the user has demonstrated an ability to locate the Query, or b) the simulation is realistically modeling the behavior of a complex system with memory, such as a human patient, and c) recall of a previously abnormal query can be erased easily by setting short durations for memory of that query, so that the user must repeatedly identify queries.

In one embodiment of the invention, a Query object comprises an attribute indicating how long to maintain the query in the system's list of abnormal queries. This memory attribute may vary from 0 to the highest allowable age of a system. In the virtual patient context, the attribute indicates how long the patient will remember to report spontaneous abnormalities in the query result.

In another embodiment of the invention, interventions supplied to a simulated patient include an attribute listing queries whose result may change when the intervention begins. For example, an intervention that causes nausea in human patients would identify the query for nausea in the intervention object's list of affected queries. This list of queries may be called a side effect list to reflect the most common use of this list in virtual patient scenarios. In one embodiment of the invention, the side effect list is maintained explicitly in a knowledge base. In another embodiment of the invention, a computer program inspecting each Query in the knowledge base to locate all linked interventions automatically generates the list.

In a further embodiment of the instant invention, system states are associated with queries whose result may suggest that the system state is present. For example, a Health State that causes abdominal pain in a human patient may be linked to a query about abdominal pain. Alternatively, the Health State may be linked to an object other than a Query, but which provides similar feedback to the user. For instance, a Health State could link to fixed text describing the usual presentation of the Health State.

For some uses, the simulator may supply interval history information to the user spontaneously, i.e., without being requested. Interval history information is an update to the user about the state of a system, including especially the status of previously discovered problems in a system, and important changes state since the last inspection. In the case of a human patient, the interval history corresponds to the broad question, "How have you been doing since our last visit?" In life, physicians and patients often recall issues reviewed at their last meeting, and can quickly resume a dialog. The virtual patient portrayed by a simulator can accomplish the same task without a Query object specifically representing the interval history. For instance, if the user received an abnormal response to a query posed during a simulated patient encounter, then the patient could spontaneously report on the status of that symptom at the next encounter. In one implementation of the invention, the simulator monitors all queries posed by a user to a virtual patient. The simulator maintains a list of queries having abnormal results for each virtual patient, defined as queries in which the logical process for assembling a response does not attain the normal response, as described above. Only queries having a memory attribute greater than zero are added to the list of queries with abnormal results. The list includes the age at which an abnormal result was last found, whether the query was automatically or manually generated. Advantageously, this allows the simulator to update the user regarding known abnormal symptoms without requiring the user to explicitly ask these questions a second time. Another advantage is that the content of the interval history message is specific to each individual user, and is therefore not a cue to pursue a particular line of reasoning.

The simulator producing an interval history uses the Query's sampling time list to calculate ages where it should sample symptom status. In one implementation of the invention, the simulator truncates the list of sampling ages at the age of the complex system at the last inspection. For instance, in the case of a human patient who is asked about the past 6 months (0.5 years) of a symptom at age 30.75 years and returns at age 31, the simulator will repeat the query but truncate the 6 month long list of sampling times to cover only 3 months (31−30.75=0.25 years=3 months) to generate the interval history.

In a separate and not mutually exclusive implementation of the invention, any intervention applied by the user to the patient may cause interval history messages. At the beginning of each new encounter, the simulator automatically evaluates all queries linked to any of a virtual patient's currently active interventions. Any abnormal result becomes a spontaneously reported new complaint. The simulator adds any Query generating such a complaint to the virtual patient's list of abnormal queries. Advantageously, this approach promptly reports medication side effects without necessarily specifying the responsible medication.

In another separate and not mutually exclusive implementation of the invention, system state changes may cause interval history messages. At the beginning of each new encounter, the simulator automatically evaluates all queries or messages linked to any Health State that is new since the last encounter. Any abnormal result becomes a spontaneously reported new complaint. The simulator adds any Query generating such a complaint to the virtual patient's list of abnormal queries. Advantageously, this approach promptly reports new symptoms without necessarily specifying the responsible Health State.

In one implementation of the invention, the simulator may remove a query with a normal result from the virtual patient's list of abnormal queries at the beginning of each encounter. If the new query result is abnormal, then the simulator stores the current age of the patient as the time of the last abnormality, and displays the result. However, if the result is normal, and the current age minus the last age of an abnormal result is greater than the memory attribute of the Query, the Query is deleted. The Query may be returned to the list whenever the Query generates an abnormal result after manual selection or after automatic selection from an active intervention's list of side effect queries.

Figure 11:
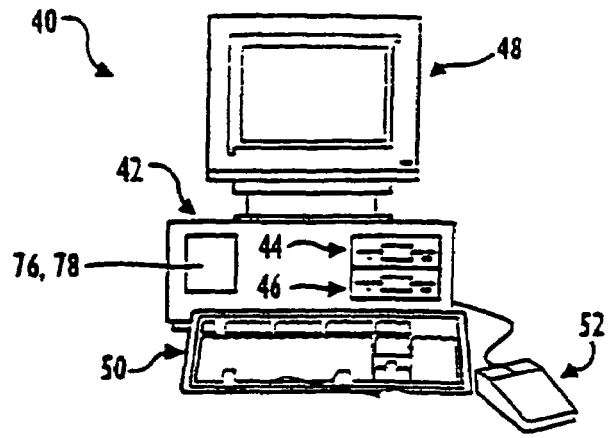
FIG. 11 is a view of a personal computer used in conjunction with the present invention.
Figure 12:
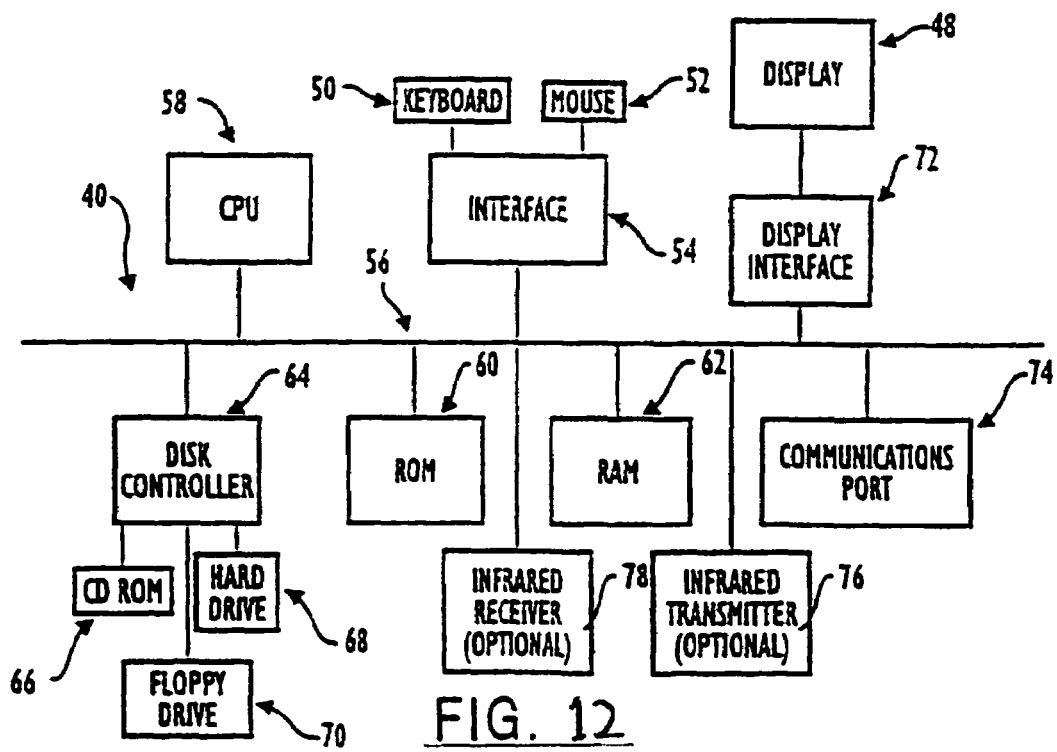
FIG. 12 is a block diagram of system architecture in accordance with one embodiment of the invention.
Figure 13:
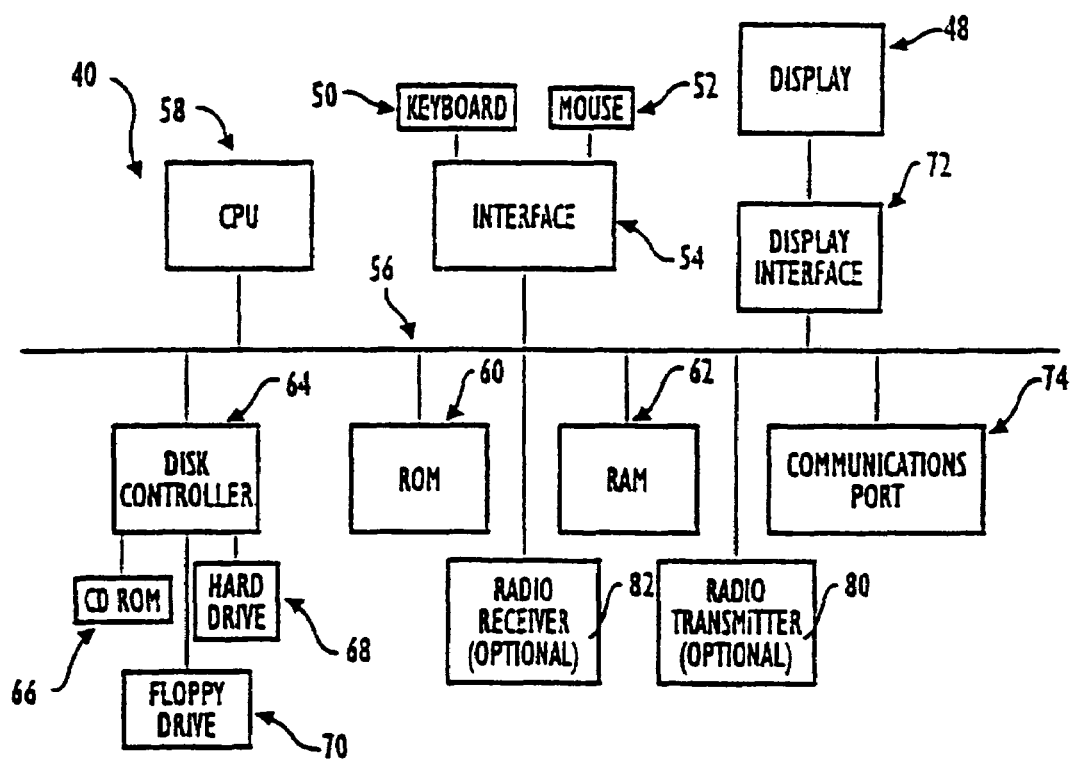
FIG. 13 is a block diagram of system architecture in accordance with one embodiment of the invention.

FIGS. 11, 12 and 13 are illustrations of exemplary computer architectures for implementing the computer processing in accordance with a computer implemented embodiment of the present invention. The procedures described above may be presented in terms of program procedures executed on, for example, a computer or network of computers. A computer system designated by reference numeral 40 has a central processing unit 42 having disk drives 44 and 46. Disk drive indication 44 and 46 are merely symbolic of a number of disk drives which might be accommodated by the computer system. Typically these would include a floppy disk drive such as 44, a hard disk drive (not shown externally) and a CD ROM indicated by slot 46. The number and type of drives varies, typically with different computer configurations. Disk drives 44 and 46 are in fact optional, and for space considerations, may easily be omitted from the computer system used in conjunction with the process/apparatus described herein.

The computer also has an optional display 48 upon which information is displayed. In some situations, a keyboard 50 and a mouse 52 may be provided as input devices to interface with the central processing unit 42. Then again, for enhanced portability, the keyboard 50 may be either a limited function keyboard or omitted in its entirety. In addition, mouse 52 may be a touch pad control device, or a track ball device, or even omitted in its entirety as well. In addition, the computer system also optionally includes at least one infrared transmitter 76 and/or infrared receiver 78 for either transmitting and/or receiving infrared signals, as described below.

Although processing system 40 is illustrated having a single processor, a single hard disk drive and a single local memory, processing system 40 may suitably be equipped with any multitude or combination of processors or storage devices. Processing system 40 may, in point of fact, be replaced by, or combined with, any suitable processing system operative in accordance with the principles of the present invention, including sophisticated calculators, and hand-held, laptop/notebook, mini, mainframe and super computers, as well as processing system network combinations of the same.

The foregoing detailed description is given primarily for clearness of understanding and no unnecessary limitations are to be understood therefrom. Modifications to the invention may be made by those skilled in the art upon reading this disclosure and without departing from the teaching of the invention and scope of the claims.

We claim:

1. A computer implemented process for generating and interacting with a multi-factoral patient simulation responsive to user queries and interventions comprising the steps of:
   a.) using a computer to generate a simulated patient, said simulated patient comprising a patient age, gender and at least one medical condition affecting the health of said patient, said at least one medical condition including a temporal component defining said patient's medical history, wherein the step of using a computer to generate a simulated patient comprises the steps of:
   1.) providing at least one first inference program describing a plurality of parallel health states of said simulated patient, wherein said plurality of parallel health states is a plurality of health states that exist simultaneously in said simulated patient;
   2.) generating with said at least one first inference program a series of time-value pairs representative of a plurality of patient symptoms at an associated time;
   b.) accepting a general query from said user regarding said patient's health;
   c.) matching the general query to at least one query object most closely associated with the general query;
   d.) using a computer to generate a symptom history of said patient, wherein the symptom history is relevant to said patient's medical condition;
   e.) generating a report summarizing the results of the symptom history of step d, wherein the details of the symptom history may include the palliation, provocation, quality, radiation, and severity and duration for each symptom;
   f.) presenting said report generated in step e to said user;
   g.) accepting a detail query from said user;
   h.) identifying any previous interventions in said patient's medical history that are relevant to said detail query;
   i.) matching said detail query to at least one query object most closely associated thereto to determine a finding related to said query, wherein said finding includes at least one pattern list, said pattern list containing trigger interventions, doses, and time-value pairs representing a physiological parameter of said patient at some time;

j.) comparing the previous interventions identified in step h with any trigger interventions identified in step i to determine whether any previous interventions are relevant to said user's detail query;

k.) producing a list of interventions relevant to said user's query and a series of time-value pairs associated with each intervention in said list;

l.) evaluating each time-value pair series in step k with a Bayesian network to determine the effects of said interventions on said patient;

m.) presenting a report to said user comprising a list of said interventions and the effects thereof on said patient.

2. A computer implemented process for generating and interacting with a multi-factorial patient simulation responsive to user queries and interventions as claimed in claim 1 wherein the step of using a computer to generate a simulated patient comprises the further steps of:

3.) providing at least one second inference program wherein the outputs of said program are associated with text phrases descriptive of said patient's symptoms;

4.) accepting the series of time-value pairs generated in step b as inputs to said at least one second inference program;

5.) assembling the text phrases associated with the outputs of said at least one second inference program to produce a report about said patient's symptoms.

3. A computer implemented process for generating and interacting with a multi-factorial patient simulation responsive to user queries and interventions as claimed in claim 2 wherein the at least one first inference program and the at least one second inference program are Bayesian networks.

4. A computer implemented process for generating and interacting with a multi-factorial patient simulation responsive to user queries and interventions as claimed in claim 1 wherein the step of accepting a general query from said user regarding said patient's health comprises the steps of:

a.) accepting a natural language query from said user;

b.) parsing said natural language query to obtain key words and phrases related to said patient's health.

5. A computer implemented process for generating and interacting with a multi-factorial patient simulation responsive to user queries and interventions as claimed in claim 1 wherein the step of using a computer to generate a symptom history of said patient is according to an entity relationship model.

6. A computer implemented process for generating and interacting with a multi-factorial patient simulation responsive to user queries and interventions as claimed in claim 5 wherein said entity relationship model comprises Patient, record, agents of change, health states, findings, queries and courses of action.

7. A computer implemented process for generating and interacting with a multi-factorial patient simulation responsive to user queries and interventions as claimed in claim 1 wherein the at least one query object comprises: a plurality of time-value pairs, a shape source for findings, a Bayesian network, a report template, and a detail list comprising palliative, provocative, qualitative, radiation, severity and duration details of said patient's symptoms.

8. A computer implemented process for generating and interacting with a multi-factorial patient simulation responsive to user queries and interventions as claimed in claim 1 wherein the report presented to said user may contain details introduced by said process having random errors within a physiologically and temporally reasonable range of values.

9. A computer implemented process for generating and interacting with a multi-factorial patient simulation responsive to user queries and interventions as claimed in claim 1 wherein the report presented to said user may contain conflicting details introduced by said process.

10. A computer implemented process for generating and interacting with a multi-factorial patient simulation responsive to user queries and interventions comprising the steps of:

a.) using a computer to generate a simulated patient, said simulated patient comprising:
   1.) a patient age;
   2.) a gender;
   3.) at least one medical condition affecting the health of said patient, said at least one medical condition represented by at least one of a plurality of parallel health states of said simulated patient, wherein said plurality of parallel health states is a plurality of health states that exist simultaneously in said simulated patient;
   4.) a list of queries likely to reveal an abnormal medical condition, each of the listed queries being a child of at least one general query, said at least one medical condition including a temporal component defining said patient's medical history;

b.) accepting a general query from said user regarding said patient's health;

c.) matching the general query to at least one query in said list that is a child of the general query; and d.) using a computer to generate a symptom history of said patient, wherein the symptom history is relevant to said patient's medical condition.

11. A computer implemented method for producing a plurality of symptom details for a simulated patient having a medical history responsive to at least one user provided query comprising the steps of:

a.) using a computer to identify physiological details of said simulated patient relevant to said at least one user provided query, wherein said physiological details are represented by at least one of a plurality of parallel health state networks of a simulated patient, wherein said plurality of parallel health state networks is a plurality of networks of health states that exist simultaneously in said simulated patient;

b.) identifying any previous interventions in said patient's medical history relevant to said at least one user provided query;

c.) identifying physiologic findings and features of said findings relevant to said at least one user provided query;

d.) identifying interventions that trigger physiological responses relevant to said at least one user provided query; and e.) identifying the timing of at least one administration of each intervention from step d), for each administration that triggers a physiological response that is present at the time of the at least one user provided query;

f.) identifying the magnitude of the physiological responses from step e) at the time of the at least one user provided query; and g.) using a computer to evaluate features identified in step d utilizing a Bayesian network to interpret said patient's symptoms.

12. In a computer implemented system for patient simulation and generation responsive to user provided queries, a process for producing a temporally reasonable response to a query from a patient physiological characteristic having at least one numeric value or from an intervention comprising the steps of:

a.) accepting a user-provided query;
b.) parsing said user-provided query using a language matching program;
c.) generating a list of at least one patient age relevant to said user provided query;
d.) using a computer to identify a numeric query object relevant to said user provided query;
e.) providing the numeric value of said at least one patient physiological characteristic as an input to the numeric query object; and
f.) using a computer to perform numeric operations on the at least one numeric value using formulas germane to the physiological characteristic to produce a response to said user provided query;

wherein said physiological characteristic is represented by at least one of a plurality of parallel health state networks of a simulated patient, wherein said plurality of parallel health state networks is a plurality of networks of health states that exist simultaneously in said simulated patient.

13. A process for generating and interpreting a multi-factoral patient simulation responsive to a user's queries and interventions comprising the steps of:
a.) generating a plurality of parallel health state networks;
b.) providing at least one first Bayesian network describing each of the plurality of parallel health state networks;
c.) providing at least one second Bayesian network describing rates of progression within and between said plurality of parallel health state networks and describing factors affecting the rates of progression;
d.) providing at least one third Bayesian network supporting query structures to limit the display of patient data to subject areas relevant to said user queries;
e.) using a computer to script a knowledge base from the at least one first Bayesian network and the at least one second Bayesian network;
f.) using a computer to generate a simulated patient having at least one medical condition affecting the health of said patient, at least in part, from the knowledge base, wherein said plurality of parallel health state networks is a plurality of networks of health states that exist simultaneously in said simulated patient;
g.) accepting at least one query from said user and matching said query to a query object;
h.) generating and displaying a detail report responsive to said at least one query;
i.) identifying prior patient interventions of interest responsive to said at least one query;
j.) accepting a user provided intervention;
k.) identifying patient physiologic findings of interest based on said at least one query, including those triggered by an intervention, by accessing said at least one third Bayesian network to determine the effects of the interventions on the patient;
l.) producing a time-value series representative of the instantiated patient's physiological response to the intervention over time;
m.) evaluating the time-value series representative of the patient's physiological response to an intervention in the at least one third Bayesian network; and
n.) generating a report listing all interventions and their effects on the patient.

14. A process for generating and interpreting a multi-factoral patient simulation responsive to a user's queries and interventions as claimed in claim 13 further comprising the step of:
a.) saving any abnormal result reported to said user responsive to said user query.

15. A process for generating and interpreting a multi-factoral patient simulation responsive to a user's queries and interventions as claimed in claim 14 further comprising the step of:
a.) automatically presenting said user with any query result reported at an immediately preceding encounter with the simulated patient wherein said previous result was abnormal.

16. A process for generating and interpreting a multi-factoral patient simulation responsive to a user's queries and interventions as claimed in claim 14 further comprising the step of:
a.) automatically presenting said user with the currently abnormal status of any query result reported at an immediately preceding encounter with the simulated patient wherein said previous result was abnormal.

17. A process for generating and interpreting a multi-factoral patient simulation responsive to a user's queries and interventions as claimed in claim 14 further comprising the step of:
a.) adjusting the period of time inspected by a query to a period no longer than the simulated time elapsed since said user's previous encounter with the simulated patient.

18. A process for generating and interpreting a multi-factoral patient simulation responsive to a user's queries and interventions as claimed in claim 14 further comprising the steps of:
a.) automatically evaluating the query producing an abnormal result reported to said user;
b.) erasing said query if said query has not evaluated to an abnormal state during a predetermined time period subsequent to the last abnormal result.

19. A process for generating and interpreting a multi-factoral patient simulation responsive to a user's queries and interventions as claimed in claim 13 further comprising the step of:
a.) providing at least one intervention, selectable by said user that influences at least one query result, such as the presence of a symptom representing a side effect of the intervention.

20. A process for generating and interpreting a multi-factoral patient simulation responsive to a user's queries and interventions as claimed in claim 19 further comprising the step of:
a.) providing a data structure describing said at least one intervention, wherein said data structure identifies at least one query result relevant thereto.

21. A process for generating and interpreting a multi-factoral patient simulation responsive to a user's queries and interventions as claimed in claim 20 further comprising the step of:
a.) automatically presenting said user with any abnormal query result identified by the at least one intervention.

22. A process for generating and interpreting a multi-factoral patient simulation responsive to a user's queries and interventions as claimed in claim 20 further comprising the step of:
a.) automatically presenting said user with any abnormal query result identified by the at least one intervention selected by said user in the preceding encounter with said simulated patient.

23. A process for generating and interpreting a multi-factoral patient simulation responsive to a user's queries and interventions as claimed in claim 20 further comprising the step of:
- a.) saving any abnormal query result identified by the at least one intervention selected by said user at a previous encounter with the simulated patient.

24. A computer implemented process for generating and interacting with a multi-factoral patient simulation responsive to user queries and interventions as claimed in claim 1 wherein the step of accepting a general query from said user regarding said patient's health further comprises parsing the general query using a language matching program.

25. A process for generating and interpreting a multi-factoral patient simulation responsive to a user's queries and interventions as claimed in claim 13 wherein said simulated patient may express preferences regarding said user provided intervention.

\* \* \* \* \*